United States Patent
Maxwell et al.

(10) Patent No.: US 11,261,424 B2
(45) Date of Patent: *Mar. 1, 2022

(54) SPERM CELL PROCESSING SYSTEMS

(71) Applicant: XY, LLC, Navasota, TX (US)

(72) Inventors: William M. C. Maxwell, Beecroft (AU); Fiona K. Hollinshead, Paddinaton (AU); Justine K. O'Brien, Paddinaton (AU); Gareth Evans, Lane Cove (AU)

(73) Assignee: XY, LLC, Navasota, TX (US)

( * ) Notice: Subject to any disclaimer, the term of this patent is extended or adjusted under 35 U.S.C. 154(b) by 336 days.

This patent is subject to a terminal disclaimer.

(21) Appl. No.: 13/765,577

(22) Filed: Feb. 12, 2013

(65) Prior Publication Data
US 2013/0158341 A1 Jun. 20, 2013

Related U.S. Application Data

(63) Continuation of application No. 11/668,148, filed on Jan. 29, 2007, which is a continuation of application
(Continued)

(51) Int. Cl.
*C12N 5/073* (2010.01)
*C12N 5/076* (2010.01)
(Continued)

(52) U.S. Cl.
CPC ............ *C12N 5/0604* (2013.01); *A61B 17/43* (2013.01); *C12N 5/061* (2013.01); *C12N 15/873* (2013.01);
(Continued)

(58) Field of Classification Search
None
See application file for complete search history.

(56) References Cited

U.S. PATENT DOCUMENTS 3,005,756 A 10/1961 VanDemark et al.
3,299,354 A 1/1967 Hogg
(Continued)

FOREIGN PATENT DOCUMENTS

BR 9704313 8/1999
CA 1029833 4/1978
(Continued)

OTHER PUBLICATIONS

Schenk JL et al. 1999. Cryopreservation of flow-sorted bovine spermatozoa. Theriogenology 52: 1375-1391.*
(Continued)

*Primary Examiner* — Sharmila G Landau
*Assistant Examiner* — Stephanie A McNeil
(74) *Attorney, Agent, or Firm* — Ryan Christensen; Hashim Rahman

(57) ABSTRACT

Semen and sperm cell processing and preservation systems, and methods of producing a mammal and methods of producing mammalian embryos are disclosed. The present invention is directed to sperm cell preservation, fertilization, and insemination, maintaining or enhancing sperm quality and addressing one or more sperm cell characteristics, such as viability, motility, functionality, fertilization rates, and pregnancy rates. Further, sperm cell characteristics may be addressed within the context of various collection, handling, separation, storage, transportation, usage, fertilization, or insemination techniques.

17 Claims, 2 Drawing Sheets

Related U.S. Application Data

No. 10/340,881, filed on Jan. 9, 2003, now Pat. No. 7,169,548.

(60) Provisional application No. 60/410,884, filed on Sep. 13, 2002.

(51) Int. Cl.
  *C12N 15/877* (2010.01)
  *C12N 15/873* (2010.01)
  *A61B 17/43* (2006.01)

(52) U.S. Cl.
  CPC ..... *C12N 15/8771* (2013.01); *C12N 15/8773* (2013.01); *A01K 2227/101* (2013.01); *A01K 2227/103* (2013.01); *C12N 2517/10* (2013.01)

(56) References Cited

U.S. PATENT DOCUMENTS

| | | | |
|---|---|---|---|
| 3,499,435 | A | 3/1970 | Rockwell et al. |
| 3,547,526 | A | 12/1970 | Devereux |
| 3,644,128 | A | 2/1972 | Lipner |
| 3,661,460 | A | 5/1972 | Elking et al. |
| 3,687,806 | A | 8/1972 | Van den Bovenkamp |
| 3,710,933 | A | 1/1973 | Fulwyler et al. |
| 3,738,759 | A | 6/1973 | Dittrich et al. |
| 3,756,459 | A | 9/1973 | Bannister |
| 3,761,187 | A | 9/1973 | Dittrich et al. |
| 3,761,941 | A | 9/1973 | Robertson |
| 3,788,744 | A | 1/1974 | Friedman et al. |
| 3,791,384 | A | 1/1974 | Richter et al. |
| 3,791,517 | A | 2/1974 | Friedman |
| 3,810,010 | A | 5/1974 | Thom |
| 3,816,249 | A | 6/1974 | Bhattacharya |
| 3,826,364 | A | 7/1974 | Bonner et al. |
| 3,829,216 | A | 8/1974 | Persidsky |
| 3,833,796 | A | 11/1974 | Fetner et al. |
| 3,854,470 | A | 12/1974 | Augspurger |
| 3,877,430 | A | 4/1975 | Wieder |
| 3,893,766 | A | 7/1975 | Hogg |
| 3,894,529 | A | 7/1975 | Shrimpton |
| 3,906,929 | A | 9/1975 | Augspurger |
| 3,909,744 | A | 9/1975 | Wisner et al. |
| 3,944,917 | A | 3/1976 | Hogg et al. |
| 3,947,093 | A | 3/1976 | Goshima et al. |
| 3,963,606 | A | 6/1976 | Hogg |
| 3,960,449 | A | 7/1976 | Carleton et al. |
| 3,973,003 | A * | 8/1976 | Colas ............ 424/561 |
| 3,973,196 | A | 8/1976 | Hogg |
| 4,006,360 | A | 2/1977 | Mueller |
| 4,007,087 | A | 2/1977 | Ericsson |
| 4,009,260 | A | 2/1977 | Ericsson |
| 4,014,611 | A | 3/1977 | Simpson et al. |
| 4,056,324 | A | 11/1977 | Gohde |
| 4,058,732 | A | 11/1977 | Wieder |
| 4,067,965 | A | 1/1978 | Bhattacharya |
| 4,070,617 | A | 1/1978 | Kachel et al. |
| 4,083,957 | A | 4/1978 | Lang |
| 4,085,205 | A | 4/1978 | Hancock |
| 4,092,229 | A | 5/1978 | Bhattacharya |
| 4,110,604 | A | 8/1978 | Haynes et al. |
| 4,148,718 | A | 4/1979 | Fulwyler |
| 4,155,831 | A | 5/1979 | Bhattacharya |
| 4,162,282 | A | 7/1979 | Fulwyler et al. |
| 4,175,662 | A | 11/1979 | Zold |
| 4,178,936 | A | 12/1979 | Newcomb |
| 4,179,218 | A | 12/1979 | Erdmann et al. |
| 4,189,236 | A | 2/1980 | Hogg et al. |
| 4,191,749 | A | 3/1980 | Bryant |
| 4,200,802 | A | 4/1980 | Salzman et al. |
| 4,225,229 | A | 9/1980 | Gohde |
| 4,225,405 | A | 9/1980 | Lawson |
| 4,230,558 | A | 10/1980 | Fulwyler |
| 4,255,021 | A | 3/1981 | Brunsden |
| 4,263,508 | A | 4/1981 | Leary et al. |
| 4,267,268 | A | 5/1981 | Nelson, Jr. |
| 4,274,408 | A | 6/1981 | Nimrod |
| 4,274,740 | A | 6/1981 | Eidenschink et al. |
| 4,276,139 | A | 6/1981 | Lawson |
| 4,302,166 | A | 11/1981 | Fulwyler et al. |
| 4,317,520 | A | 3/1982 | Lombardo et al. |
| 4,318,480 | A | 3/1982 | Lombardo et al. |
| 4,318,481 | A | 3/1982 | Lombardo et al. |
| 4,318,482 | A | 3/1982 | Barry et al. |
| 4,325,483 | A | 4/1982 | Lombardo et al. |
| 4,327,177 | A | 4/1982 | Shrimpton |
| 4,339,434 | A | 7/1982 | Ericsson |
| 4,341,471 | A | 7/1982 | Hogg et al. |
| 4,348,107 | A | 9/1982 | Leif |
| 4,350,410 | A | 9/1982 | Minott |
| 4,352,558 | A | 10/1982 | Eisert |
| 4,361,400 | A | 11/1982 | Gray et al. |
| 4,362,246 | A | 12/1982 | Adair |
| 4,367,043 | A | 1/1983 | Sweet et al. |
| 4,395,397 | A | 7/1983 | Shapiro |
| 4,395,676 | A | 7/1983 | Hollinger et al. |
| 4,400,764 | A | 8/1983 | Kenyon |
| 4,408,877 | A | 10/1983 | Lindmo et al. |
| 4,422,761 | A | 12/1983 | Frommer |
| 4,448,767 | A | 5/1984 | Bryant |
| 4,474,875 | A | 10/1984 | Shrimpton |
| 4,487,320 | A | 12/1984 | Auer |
| 4,492,436 | A | 1/1985 | Bergmann |
| 4,498,766 | A | 2/1985 | Unterleitner |
| 4,501,366 | A | 2/1985 | Thompson |
| 4,511,661 | A | 4/1985 | Goldberg |
| 4,515,274 | A | 5/1985 | Hollinger et al. |
| 4,523,809 | A | 6/1985 | Toboada et al. |
| 4,545,677 | A | 10/1985 | Chupp |
| 4,538,733 | A | 11/1985 | Hoffman |
| 4,559,309 | A | 12/1985 | Evenson |
| 4,573,796 | A | 3/1986 | Martin |
| 4,585,736 | A | 4/1986 | Dolbeare et al. |
| 4,598,408 | A | 7/1986 | O'Keefe |
| 4,600,302 | A | 7/1986 | Sage, Jr. |
| 4,605,558 | A | 8/1986 | Shrimpton |
| 4,609,286 | A | 9/1986 | Sage, Jr. |
| 4,629,687 | A | 12/1986 | Schindler et al. |
| 4,631,483 | A | 12/1986 | Proni et al. |
| 4,637,691 | A | 1/1987 | Uehara et al. |
| 4,654,025 | A | 3/1987 | Cassou et al. |
| 4,659,185 | A | 4/1987 | Aughton |
| 4,660,971 | A | 4/1987 | Sage et al. |
| 4,661,913 | A | 4/1987 | Wu et al. |
| 4,662,742 | A | 5/1987 | Chupp |
| 4,673,288 | A | 6/1987 | Thomas et al. |
| 4,673,289 | A | 6/1987 | Gaucher |
| 4,680,258 | A | 7/1987 | Hammerling et al. |
| 4,683,195 | A | 7/1987 | Mullis et al. |
| 4,683,202 | A | 7/1987 | Mullis |
| 4,691,829 | A | 9/1987 | Auer |
| 4,698,142 | A | 10/1987 | Muroi et al. |
| 4,702,598 | A | 10/1987 | Bohmer |
| 4,704,891 | A | 11/1987 | Recktenwald et al. |
| 4,710,635 | A | 12/1987 | Chupp |
| 4,714,680 | A | 12/1987 | Civin |
| 4,737,025 | A | 4/1988 | Steen |
| 4,744,090 | A | 5/1988 | Freiberg |
| 4,749,458 | A | 6/1988 | Muroi et al. |
| 4,752,131 | A | 6/1988 | Eisenlauer et al. |
| 4,756,427 | A | 7/1988 | Gohde et al. |
| 4,758,729 | A | 7/1988 | Monnin |
| 4,764,013 | A | 8/1988 | Johnston |
| 4,765,737 | A | 8/1988 | Harris et al. |
| 4,770,992 | A | 9/1988 | den Engh et al. |
| 4,778,593 | A | 10/1988 | Yamashita et al. |
| 4,780,406 | A | 10/1988 | Dolbeare et al. |
| 4,780,451 | A | 10/1988 | Donaldson |
| 4,786,165 | A | 11/1988 | Yamamoto et al. |
| 4,790,653 | A | 12/1988 | North, Jr. |
| 4,794,086 | A | 12/1988 | Kasper et al. |
| 4,796,788 | A | 1/1989 | Bond |
| 4,818,103 | A | 4/1989 | Thomas et al. |
| 4,831,385 | A | 5/1989 | Archer et al. |

(56) References Cited

U.S. PATENT DOCUMENTS

| | | |
|---|---|---|
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,057,420 A * | 10/1991 | Massey .................. 800/24 |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,434,058 A * | 7/1995 | Davidson .................. 435/69.1 |
| 5,437,987 A | 8/1995 | Ten et al. |
| 5,439,362 A | 8/1995 | Spaulding |
| 5,444,527 A | 8/1995 | Kosaka |
| 5,447,841 A | 9/1995 | Grey et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,578,449 A | 11/1996 | Fr asch et al. |
| 5,579,159 A | 11/1996 | Ito |
| 5,584,982 A | 12/1996 | Dovichi et al. |
| 5,589,457 A | 12/1996 | Wiltbank |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Grouley et al. |
| 5,620,842 A | 4/1997 | Davis et al. |
| 5,622,820 A | 4/1997 | Rossi |
| 5,627,037 A | 5/1997 | Ward et al. |
| 5,633,076 A * | 5/1997 | DeBoer et al. .................. 800/25 |
| 5,633,503 A | 5/1997 | Kosaka |
| 5,641,457 A | 6/1997 | Vardanega |
| 5,643,796 A | 7/1997 | den Engh et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,700,692 A | 12/1997 | Sweet |
| 5,701,012 A | 12/1997 | Ho |

(56) References Cited

U.S. PATENT DOCUMENTS

| | | |
|---|---|---|
| 5,707,808 A | 1/1998 | Roslaniec et al. |
| 5,708,868 A | 1/1998 | Ishikawa |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | den Engh et al. |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,795,767 A | 8/1998 | Lakowicz et al. |
| 5,796,112 A | 8/1998 | Ichie |
| 5,798,276 A | 8/1998 | Haugland et al. |
| 5,815,262 A | 8/1998 | Schrof et al. |
| 5,799,830 A | 9/1998 | Carroll et al. |
| 5,804,436 A | 9/1998 | Okun et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,712,807 A | 12/1998 | Bangham |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Paisson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,204,431 B1 | 3/2001 | Prieto et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan et al. |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,395,305 B1 | 5/2002 | Buhr et al. |
| 6,411,904 B1 | 5/2002 | Chandler |
| 6,400,453 B1 | 6/2002 | Hansen |
| 6,411,835 B1 | 6/2002 | Modell et al. |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Karsten et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |
| 6,587,203 B2 | 7/2003 | Colon |

(56) References Cited

U.S. PATENT DOCUMENTS

| | | |
|---|---|---|
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B1 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,704,313 B1 | 3/2004 | Duret et al. |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 4/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,759 B2 | 9/2004 | Heldt |
| 6,793,387 B1 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozenboom et al. |
| 6,849,423 B2 | 2/2005 | Mutz et al. |
| 6,861,265 B1 | 3/2005 | den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 | 9/2006 | Kurabayashi et al. |
| 7,169,548 B2 | 1/2007 | Maxwell et al. |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0129091 A1 | 1/2003 | Seidel et al. |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0107150 A1 | 6/2004 | Neas et al. |
| 2004/0132001 A1 | 7/2004 | Seidel et al. |
| 2005/0003472 A1 | 1/2005 | Muhammad |
| 2005/0011582 A1 | 1/2005 | Haug |
| 2005/0112541 A1 | 5/2005 | Durack |
| 2005/0214733 A1 | 9/2005 | Graham |
| 2005/0244805 A1 | 11/2005 | Ludwig et al. |
| 2005/0282245 A1 | 12/2005 | Ludwig et al. |
| 2006/0118167 A1 | 6/2006 | Neas et al. |
| 2006/0147894 A1 | 7/2006 | Sowter |
| 2006/0263829 A1 | 11/2006 | Evans et al. |
| 2006/0281176 A1 | 12/2006 | Seidel et al. |
| 2007/0026378 A1 | 2/2007 | Schenk |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0017086 A1 | 5/2007 | Evans et al. |
| 2007/0099171 A1 | 5/2007 | Schenk |
| 2007/0099260 A1 | 5/2007 | Seidel et al. |

FOREIGN PATENT DOCUMENTS

| | | |
|---|---|---|
| CA | 1 250 808 | 3/1989 |
| CA | 2113957 A1 | 1/1994 |
| CN | 03109426.0 | 12/2005 |
| EP | 0 026 770 B1 | 3/1963 |
| EP | 0025296 A2 | 3/1981 |
| EP | 0 046 345 A2 | 2/1982 |
| EP | 0 068 404 B1 | 1/1983 |
| EP | 0071538 A1 | 2/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A1 | 3/1993 |
| EP | 0538786 A | 4/1993 |
| EP | 0 279 000 B1 | 7/1993 |
| EP | 0 553 951 A1 | 8/1993 |
| EP | 0 288 029 B1 | 1/1994 |
| EP | 0 381 694 B1 | 6/1994 |
| EP | 0 361 504 B1 | 7/1994 |
| EP | 606847 A2 | 7/1994 |
| EP | 0 289 200 B2 | 8/1994 |
| EP | 0 555 212 B1 | 10/1994 |
| EP | 0 361 503 B1 | 11/1994 |
| EP | 0 696 731 A2 | 2/1996 |
| EP | 0 705 978 A2 | 4/1996 |

(56) References Cited

FOREIGN PATENT DOCUMENTS

| | | |
|---|---|---|
| EP | 0 711 991 A1 | 5/1996 |
| EP | 0 471 758 B1 | 9/1996 |
| EP | 0 736 765 A1 | 10/1996 |
| EP | 0 545 284 B1 | 2/1997 |
| EP | 0 360 487 B1 | 7/1997 |
| EP | 0 412 431 B1 | 10/1997 |
| EP | 0 526 131 B1 | 1/1998 |
| EP | A-0 478155 | 1/1998 |
| EP | 0 822 404 A3 | 2/1998 |
| EP | 0 822 401 A2 | 4/1998 |
| EP | 0 556 748 B1 | 10/1998 |
| EP | 0 430 402 B1 | 1/1999 |
| EP | 0 529 666 B1 | 4/2000 |
| EP | 0 994 342 A3 | 4/2000 |
| EP | 0 752 133 B1 | 6/2000 |
| EP | 1 018 644 A2 | 7/2000 |
| EP | 1 118 268 A1 | 7/2001 |
| EP | 1 147 774 A1 | 10/2001 |
| EP | 0 534 033 B1 | 11/2001 |
| EP | 0 925 494 B1 | 12/2001 |
| EP | 0 748 316 B1 | 5/2002 |
| EP | 0 662 124 B1 | 6/2002 |
| EP | 1 245 944 A3 | 10/2002 |
| EP | 1 249 502 A2 | 10/2002 |
| EP | 1250897 A1 | 10/2002 |
| EP | 1 380 304 A2 | 1/2004 |
| EP | 1403633 A3 | 4/2004 |
| EP | 1 100 400 B1 | 5/2004 |
| EP | 1 257 168 B1 | 2/2005 |
| FR | 2574656 A1 | 6/1988 |
| FR | A-2 635453 | 2/1990 |
| FR | 2 647 668 A | 12/1990 |
| FR | 2699678 A1 | 6/1994 |
| GB | 1471019 | 4/1977 |
| GB | 2 121 976 A | 1/1984 |
| GB | 2 122 369 A | 1/1984 |
| GB | 2 125 181 A | 2/1984 |
| GB | 2 136 561 A | 9/1984 |
| GB | 2 137 352 A | 10/1984 |
| GB | 2145112 | 2/1985 |
| GB | 2 144 542 A | 3/1985 |
| GB | 2 153 521 A | 8/1985 |
| GB | 2 243 681 A | 11/1991 |
| GB | 2 360 360 A | 9/2001 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| SU | 1056008 | 11/1983 |
| SU | 1260778 A1 | 9/1986 |
| WO | WO 84/01265 A1 | 4/1984 |
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 90/13315 A1 | 11/1990 |
| WO | WO 199105236 | 4/1991 |
| WO | WO 92/08120 A1 | 5/1992 |
| WO | WO 92/17288 A1 | 10/1992 |
| WO | WO 93/10803 | 6/1993 |
| WO | WO 93/17322 A1 | 9/1993 |
| WO | WO 94/22001 A1 | 9/1994 |
| WO | WO 96/04542 A1 | 2/1996 |
| WO | WO 96/12172 | 4/1996 |
| WO | WO 96/12173 A1 | 4/1996 |
| WO | WO 96/31764 | 10/1996 |
| WO | WO 96/33806 A1 | 10/1996 |
| WO | WO 97/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 89/04472 A1 | 5/1998 |
| WO | WO 98/48259 | 10/1998 |
| WO | WO 98/57152 A1 | 12/1998 |
| WO | 99/33956 A1 | 7/1999 |
| WO | 1999/033956 | 7/1999 |
| WO | WO 99/44035 | 9/1999 |
| WO | WO 99/44037 A1 | 9/1999 |
| WO | WO 99/47906 A1 | 9/1999 |
| WO | WO 99/60397 A1 | 11/1999 |
| WO | WO 9957955 | 11/1999 |
| WO | WO 99/61888 A2 | 12/1999 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/70080 | 11/2000 |
| WO | WO 01/02836 A1 | 1/2001 |
| WO | WO 01/28700 A1 | 4/2001 |
| WO | WO 2001029538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/42757 A2 | 6/2001 |
| WO | WO 0151612 A1 | 7/2001 |
| WO | WO 01/61313 A2 | 8/2001 |
| WO | WO 01/68110 | 9/2001 |
| WO | WO 01/68226 A2 | 9/2001 |
| WO | WO 01/71348 A1 | 9/2001 |
| WO | WO 0175176 | 10/2001 |
| WO | WO 01/85913 A2 | 11/2001 |
| WO | WO 01/85913 A3 | 11/2001 |
| WO | WO 01/90295 A1 | 11/2001 |
| WO | WO 2002041906 A2 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 | 3/2002 |
| WO | WO 02/19943 A1 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 02/26114 A2 | 4/2002 |
| WO | WO 02/29106 A2 | 4/2002 |
| WO | WO 0228311 A2 | 4/2002 |
| WO | WO 02/41906 A2 | 5/2002 |
| WO | WO 02/43486 A1 | 6/2002 |
| WO | WO 02/44319 A2 | 6/2002 |
| WO | WO 0243574 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A1 | 8/2002 |
| WO | WO 2003020877 A2 | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03/056330 A2 | 7/2003 |
| WO | WO 03/056335 A2 | 7/2003 |
| WO | WO 03/ 072765 A1 | 9/2003 |
| WO | WO 03/078065 A1 | 9/2003 |
| WO | WO 03/078972 A1 | 9/2003 |
| WO | WO 04001401 | 12/2003 |
| WO | WO 04/009237 A2 | 1/2004 |
| WO | WO 04/009237 A3 | 1/2004 |
| WO | WO 2004/006916 A1 | 1/2004 |
| WO | WO 04/012837 A2 | 2/2004 |
| WO | WO 04/012837 A3 | 2/2004 |
| WO | WO 04/017041 A2 | 2/2004 |
| WO | WO 04/017041 A3 | 2/2004 |
| WO | WO 04/024227 A2 | 3/2004 |
| WO | WO 04/024227 A3 | 3/2004 |
| WO | WO 2004/046712 A2 | 6/2004 |

(56) References Cited

FOREIGN PATENT DOCUMENTS

| WO | WO 2004/059282 A2 | 7/2004 |
|---|---|---|
| WO | WO 2004/003697 A2 | 10/2004 |
| WO | WO 2004/087177 A1 | 10/2004 |
| WO | WO 2004/088283 A2 | 10/2004 |
| WO | WO 04/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006060770 A2 | 8/2006 |
| WO | WO 2007016090 A2 | 2/2007 |
| WO | WO 01/75161 A2 | 10/2011 |

OTHER PUBLICATIONS

Nakagata N et al. 1997. Positive Effect of Partial Zona-Pellucida Dissection on the In Vitro Fertilizing Capacity of Cryopreserved C57BL/6J Transgenic Mouse Spermatozoa of Low Motility. Biol Reprod 57: 1050-1055.*
Sztein JM et al. 2000. In Vitro Fertilization with Cryopreserved Inbred Mouse Sperm. Biol Reprod 63: 1774-1780.*
"Sexing Technologies: History." Available online at <http://www.sexingtechnologies.com/articles/history>. Accessed Jun. 22, 2016.*
"XY LLC." Available online at <http://www.xy-llc.com/index.php>. Accessed Jun. 22, 2016.*
"Assignment Details 30105-360: Change of Name." Available online at <http://assignment.uspto.gov/#/assignment?id=30105-360&q=XY%20AND%20applNum%3A(13765577)>. Accessed Jun. 22, 2016.*
Olson et al., Culture of In Vitro-Produced Bovine Embryos with Vitamin E Improves Development In Vitro and After Transfer to Recipients, 2000, Biology of Reproduction 62: 248-252 (Year: 2000).*
Fugger et al., "Births of normal daughters after MicroSort sperm separation and intrauterine insemination, in-vitro fertilization, or intracytoplasmic sperm injection" 1998, vol. 13, No. 9, 2367-2370.
U.S. office action dated Feb. 24, 2010 in corresponding U.S. Appl. No. 11/668,148.
U.S. final office action dated Jul. 20, 2010 in corresponding U.S. Appl. No. 11/668,148.
U.S. Appl. No. 11/668,148.
U.S. Appl. No. 10/340,881 (now granted U.S. Pat. No. 7,169,548).
Canadian Notice of Allowance dated Aug. 6, 2013 issued in corresponding CA Application No. 2538118 (1 pages).
G.E.Seidel, Jr. et al., Theriogenology, vol. 51, No. 1, Jan. 1, 1999, p. 400.
Fugger et al. Births of normal daughters after MicroSort sperm separation and intrauterine insemination, in-vitro fertilization, or intracytoplasmic sperm injection. Human Reproduction, Sep. 1998, vol. 13, No. 9, pp. 2367-2370.
Corresponding Canadian Patent Appl. No. 2,538,118; Examination Report dated Jul. 11, 2012, 2 total pages.
Corresponding European Patent Appl. No. 10186250.6; Office Action dated Mar. 21, 2012, 11 total pages.
Corresponding Mexican Patent Appl. No. PA/a/2002/005134; Office Action dated Sep. 26, 2011, 2 total pages.
Corresponding Australian Patent Appl. No. 2011201281; Office Action dated Oct. 4, 2011, 2 total pages.
Corresponding U.S. Appl. No. 12/853,196; Office Action dated Dec. 1, 2011, 17 total pages.
Corresponding Canadian Patent Appl. No. 2,538,118; Office Action dated Jun. 6, 2011, 3 total pages.
Abeydeera et al. Birth of Piglets Preselected for Gender Following In Vitro Fertilization on In Vitro Matured Pig Oocytes by X and Y Chromosome Dearing Spermatozoa Sorted by High Speed Flow Cytometry. Theriogenology 50: 981-988, 1998.
Parallel European Application No. 03795716.4, Notice of Intent to Grant dated Feb. 25, 2011, 4 pages.
Parallel Canadian application No. 2,538,118, Office Action dated Jul. 6, 2010, 6 pages.
Parallel New Zealand application No. 571126, Office Action dated May 28, 2010, 3 pages.
Parallel Australian application No. 2003277099, Notice of Acceptance with allowed claims dated Oct. 20, 2009, 10 pages.
Parallel Chinese application No. 038217538, Notice of Allowance with allowed claims dated Oct. 21, 2009, 9 pages.
Dalton et al., The Effect of Time of Artificial Insemination on Fertilization Status and Embryo Quality in Superovulated Cows. J Anim Sci, 2000; 78, pp. 281-285.
Elsden et al., Non-Surgical Recovery of Bovine Eggs. Theriogenology, Nov. 1976; vol. 6, No. 5; pp. 523-532.
Hawk at al., Effect of Unilateral Cornual Insemination upon Fertilization Rate in Superovulating and Single-Ovulating Cattle. J Anim Sci, 1986; 63, pp. 551-560.
Parallel New Zealand Patent Application No. 539388; Office Action dated Sep. 15, 2008.
Parallel New Zealand Patent Application No. 539388; Office Action dated Sep. 29, 2008.
Parallel New Zealand Patent Application No. 539388; Office Action dated Jan. 27, 2009.
Parallel New Zealand Patent Application No. 539388; Notice of Acceptance of Complete Specification dated Feb. 24. 2009.
Parallel New Zealand Patent Application No. 539388; Acceptance of Application dated Mar. 25, 2009.
Parallel New Zealand Patent Application No. 571126; Office Action dated Sep. 15, 2008.
Buchanan, B.R. "Pregnancy Rates in Mares Following a Single Insemination with a Low Number of Spermatozoa into the Tip of the Uterine Horn" Theriogenology p. 395 1999.
Celestron: Telescope Basics: www.celestron.com/tb-2ref/htm; 4 pages, Oct. 20, 2003.
Herzenberg, Leonard A. "Flourescence-activated Cell Sorting," Sci. Am. 1976; 234, pp. 108-117.
Horan, Paul K. "Quantitative Single Cell Ana,lysis and Sorting, Rapid Analysis and sorting of cells is emerging as an important new technology in research and medicine." Science, Oct. 1977.
Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.
Moe, P. W., "Energetics of Body Tissue Mobilization." J. of Dairy Sci. 1971 54:548.
O'Brien, Justine K. et al., "Preliminary Developments of Sperm Sorting Technology in Non-human Primates", Biology of Reproduction 2001 (Suppl. 1) 64:158.
Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 2001, 23:115-121.
Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).
Bavister, B.D. et al.. The effects of Sperm Extracts and Energy Sources on the Motility and Acromosome Reaction of hamster Spermatozoa in vitero; Biology of Reproduction 16, 228 237 (1997).
Fattouh, El-S.M. et al., Effect of Caffine on the Post-Thaw Motility of Buffalo Spermatozoa; Theriogenology, Jul. 1991, vol. 36 No. 1.
Koh-ichi Hamano, et al., Gender Preselection in Cattle with Intracytoplasmically injected, flow cytometrically sorted sperm heads, Biology of Reporduction 60, 1194-1197 (1990).
Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.
Nikkei Biotech, Supplement, Latest Information of Biological Instruments and Reagents, 1988, pp. 93-94.

(56) References Cited

OTHER PUBLICATIONS

Pursley, J.R. et al., Reproductive Management of Lactating Dairy Cows Using Synchronization of Ovulation; 1997 J. Dairy Sci 80:301-306.
Bagnato, A., Genetic and Breeding; Phenotypic Evaluation of Fertility Traits and Their Association with Milk Production of Italian Friesian Cattle; 1994 J. Dairy Sci 77:874-882.
Panskowski, J., A., et al. Use of Prostaglandin F2a as a Postpartum Reproductive Management Tool for Lactating Dairy Cows; 1995 J. Dairy Sci 78:1477-1488.
Scipioni, R. L., et al., Short Communication: An Electronic Probe Versus Milk Protesterone as Aids for Reproductive Management of Small Dairy Herds; 1999 J. Dairy Sci 82:1742-1745.
Fricke, P. M., Scanning the Fugure—Ultrasonography as a Reproductive Management Tool for Dairy Cattle; J. Dairy Sci 85:1918-1926.
Grant, V. J., et al., Sex-Sorted Sperm and Fertility: An Alternative View; Biology of Reproduction 76, 184-188 (2007).
Garner, D. L., Sex-Sorting Mamallian Sperm: Concept to Application in Aminals; Journal of Andrology, vol. 22, No. 4 Jul./Aug. 2001.
Tubman, L.M. et al., Characteristics of calves produced with sperm sexed by flow cytometry/cell sorting; 2004 Amer. Society of Animal Sciences; 82:1029-1036.
Weigel, K. A., Exploring the Role of Sexed Semen in Dairy Production Systems; J. Dairy Sci. 87: (E.Suppl.): E120-E130; 2004 American Dairy Science Assoc.
Ferre, L., In vitro-derived embryo production with sexed and unsexed semen from different bulls; Reproduction Fertility and Development, vol. 16, Part 1/2, p. 253, 2004.
Dalton, J.C., et al., Effect of Time of Insemination on Number of Accessory Sperm, Fetilization Rate, and Embryo Quality in Nonlactating Dairy Cattle. J Dairy Sci. 84:2413-2418.
Dransfield, M.B.G., et al., Timing of Inseminatio for Dairy Cows Identified in Estrus by a Radiotelemetric Etrus Detection System. 1998 J Dairy Sci. 81: 1874-1882.
Maatje, K. et al. Predicting Optimal Time of Insemination in Cows that Show Visual Signs of Estrus by Estimating onset of Estrus with Pedometers.
Nebel, R.L. et al. Timing of Artificial Insemination of Dairy Cows: Fixed Time Once Daily Versus Morning and Afternoon 1994 J Dairy Sci. 77:3185-3191.
Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.
Rozeboom, K. J. et al. Late Estrus or Metestrus Insemination After Estrual Inseminations Decreases Farrowing Rate and Litter Size in Swine J. Animal Sci. 1997. 75: 2323-2327.
Peeler, I. D. et al. Pregnancy Rates After Times Al of Heifers Following Removal of Intravaginal Progesterone Inserts, J. Dair Sci., 87:2868-2873; 2004.
Rath, D. Low Dose Insemination in the Sow—A Review, Reprod. Dom Anim. 37, 201-205 (2002) www.blackwell.de/synergy.
Lukaszewicz, M. et al. Attempts on freezing the Greylag (*Anser anser* L.) gander semen Animal Reproduction Science 80 (2004) 163-173.
Foote, R. H. et al. Sperm Numbers Inseminated in Dairy Cattle and Nonreturn Rates Revisited 1997 J Dairy Science 80:3072-3076.
Conley, H.H. et at. Intensification by Intrauterine Devices of Sperm Loss from the Sheep Uterus Biology of Reproduction 2, 401-407 (1970).
Chrenek, Peter et al. Fertilizing Capacity of Transgenic and Non-Transgenic Rabbit Spermatozoa after Heterospermic Insemination Bull Vet. Inst. Pulawy 49, 307-310, 2005.
Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.
Pursel, V. G., et al. Distribution and morphology of fresh and frozen-thawed sperm in the reproductive tract of gilts after artificial insemination; Biology of Reproduction 19, 69-76 (1978).
Rath, D., "On the Status of Sex-Specific Sperm Sorting" Review lecture ET Conference 2002, Department of Animal Production and Animal Behaviour, Mariensee, Germany.
De Graaf, S.P. et al., Birth of offspring of pre-determined sex after artificial insemination of frozen-thawed, sex-sorted and re-frozen-thawed ram spermatozoa, Theriogenology, 67 (2007) 391-398.
O'Brien, J.K. et al., Development fo sperm sexing and associated assisted reproductive technology for sex preselection of captive bottlenose dolphins, Reproduction Fertility and Development, 2006, 18, 319-329.
Zhang, M, et al., In vitro fertilization with flow-sorted buffalo sperm, Reproduction Fertility and Development, 2005, 18(2), 283-284.
Schenk, J.L. et al., Insemination of cow elk with sexed frozen semen, 2003 Theriogenology 59, 514.
BD Biosciences Brochure, BD FACSCalibur Flow Cytometer, the Automated, Multicolor Flow Cytometry System, 2006.
Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.
Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.
Presicce, G.A., et al., First established pregnancies in mediterranean Italian buffaloes (*Bubalus bubalis*) following deposition of sexed spermatozoa near the utero tubal junction, Reproduction in Domestic Animals, vol. 40, No. 1, Feb. 2005 , pp. 73-75(3).
Dielemann, S.J., Superovulation in cattle: from understanding the biological mechanisms to genomics of the oocyte; $23^{rd}$ Annual Meeting A.E.T.E.—Alghero; Sep. 2007.
Hasler, J. F., Factors influencing the success of embryo transfer in cattle; $23^{rd}$ World Buiatrics Congress, Quebec, Canada Jul. 2004.
Mapletoft, R. J. et al., Superovulation in perspective, Bioniche Animal Health, Dec. 2002.
Bahr, G.F.et al., Considerations of volume, mass, DNA, and arrangement of mitochondria in the midpiece of bull spermatozoa, Experimental Cell Research 60 (1970) 338-340.
Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.
Bermudez, D.et al., The immediate effect of IR, laser radiation on rat, germ, cells, was studied by cytophotometric quantification, Scisearch 2001.
Sequent Biotechnologies Inc., Welcome to the Sequent Biotechnologies Inc. website., http://www.sequentbiotech.com/ Dec. 6, 2003.
Sabuer K. et al."Effects of Angiotensin II on the Acrosome Reaction in Equine Spermatozoa" Journal of Reproduction and Fertility vol. 120, 2002 p. 135-142.
Brooks, D.E., Manipulation of Mammalian Gametes in Vitro, Biennial Report, Waite Agricultural Research Institute 1986-1989.
Bruemmer, J.E. et al., "Effect of Pyruvate on the Function of Stallion Spermatozoa Stored for up to 48 Hours", Journal of Animal Science 2002, vol. 80*1, pp. 12-18.
Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).
Chaudhry, P. et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.
Chen, Y. et al., Effects of sucrose, trehalose, hypotaurine, taurine, and blood serum on survival of frozen bull sperm, Cryobiology 30,423-431 (1993).
Chapter 16 Semen processing, storage, thawing, and handling, http://nongae.gsnu.ac.kr/~cspark/teaching/chap16.html Sep. 23, 2002.

(56) References Cited

OTHER PUBLICATIONS

Conover, J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).
Cressman, B.E. MD, et al., Effect of sperm dose on pregnancy rate from intrauterine insemination: a retrospective analysis, Texas Medicine, 92:74-79 (1996).
Crissman, H.A. et al., Use of DIO-C5-3 to improve hoechst 33342 uptake, resolution of DNA content, and survival of CHO cells, Experimental cell research 174: 338-396 (1988).
Graves, C.N., et al., "Metabolism of Pyruvate by Epididymal-Like Bovine Spermatozoa", 1964 Journal of Dairy Science vol. 47 (12), pp. 1407-1411.
Certified Semen Services, CSS Minimum requirements for disease control of semen produced for AI, http://www.naab-css.org/about_css/disease_control-2002.html Sep. 22, 2003.
Culling, "Handbook of Histopathological and Histochemical Techniques, "3rd Ed., Butterworths, pp. 192.
De Grooth, B. et al., Simple delay monitor for droplet sorters, Cytometry 12:469-472 (1991).
Lodge, J.R., et al., "Carbon Dioxide in Anaerobic Spermatozoan Metabolism" 1968, Journal of Dairy Science, vol. 51(1), pp. 96-103.
Delgado, N. et al., Correlation between sperm membrane destabilization by heparin and aniline blue staining as membrane integrity index, Archives of Andrology 40:147-152 (1998).
Denniston, D.J. et al., "Effect of Antioxidants on the Motility and Viability of Cooled Stallion Spermatozoa", Journal Reproduction Supplement 56, 2001, pp. 121-126.
De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.
Donoghue, A. et al., Effects of water- and lipid-soluble antioxidants on turkey sperm viability, membrane integrity, and motility during liquid storage, Poultry Science 76:1440-1445 (1997).
Zucker, R. et al.. Utility of light scatter in the Morphological analysis of sperm, Cytometry 13:39-47 (1992).
Ericsson, S. et al., Interrelationships among fluorometric analyses of spermatozoal function, classical semen quality parameters and the fertility of frozen—thawed bovine spermatozoal, Theriogenology 39:1009-1024 (1993).
Ericsson, et al. "Flow Cytometric Evaluation of Cryopreserved Bovine Spermatozoa Processed Using a New Antiobiotic Combination", Theriogenology, 1990, vol. 33(6), pp. 1211-1220.
Esteves, S et al., Improvement in motion characteristics and acrosome status in cryopreserved human spermatozoa by swim-up processing before freezing, Human Reproduction vol. 15 No. 10 pp. 2173-2179 (2000).
Evenson, D. et al., Physiology and Management, Rapid determination on sperm cell concentration in bovine semen by flow cytometry, J Dairy Sci. 76: 86-94 (1993).
Farrell et al., "Quantification of Bull Sperm Characteristics measured by Computer-Assisted Sperm Analysis (CASA) and the Relationship of Fertility", Theriogenology, 1998, vol. 49 (4), pp. 871-879.
Foote, R., The history of artificial insemination: Selected notes and notables, American Society of Animal Science (2002).
Johnson, L. et al., Recent advances in sex preselection of cattle: Flow cytometric sorting of X-&Y-chromosome bearing sperm based on DNA to produce progeny, Theriogenology 41:51-56 (1994).
Ashwood-Smith, M., Debate Human sperm sex selection, Human Reproduction vol. 9 No. 5 pp. 757-759 ( 1994).
Pinkel, D.et al.,Flow cytometry of mammalian sperm progress in DNA and morphology measurement, The Journal of Histochemical and Cytochemistry vol. 27 No. 1 pp. 353-358 (1979).
Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.
Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).
Salisbury, G.W., et al., Reversal by Metabolic Regulators of CO2-induced Inhibition of Mammalian Spermatozoa, 1959, Proc Soc Exp Biology Med, vol. 101 (1) pp. 187-189.
Bencic, D.C., et al., "Carbon Dioxide Reversibly Inhibits Sperm Motility and Fertilizing Ability in Steelhead (*Oncorhynchus mykiss*)" 2000, Fish Physiology and Biochemistry, vol. 23(4), pp. 275-281.
Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.
Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.
Eiman, M et al., Trehalose-enhanced fluidity of the goat sperm membrane and its protection during freezing, Biology of Reproduction 69: 1245-1250 (2003).
Foote, R.et al., Physiology and Management, Fertility of bull spermatozoa frozen in whole milk extender with trehalose, taurine, or blood serum, J. Dairy Sci. 76:1908-1913 (1993).
Johnson, L. et al., Storage of bull semen, Animal Reproduction Science 62:143-172 (2000).
Johnson, L. et al.,Erratum to "Storage of bull semen", Animal Reproduction Science 62: 143-172 (2000).
McNutt,T.et al., Electrophoretic gel analysis of Hoechst 33342 stained and flow cytometrically sorted bovine sperm membrane proteins, Reprod. Dom Anim.31: 703-709 (1996).
Best, T. P. et al. "Nuclear Localization of Pyrrole-Imidazole Ployamide-Flourescein Conjugates in Cell Culture", PNAS, 2003, vol. 100(21), pp. 12063-12068.
Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.
Anzar, M.et al., Optimizing and Quantifing fusion of liposomes to mammalian sperm using resonance energy transfer and flow cytometric methods, Cytometry 49:22-27 (2002).
Anzar, M.et al., Sperm Apoptosis in fresh and cryopreserved bull semen detected by flow cytometry and it's relationship with fertility, Biology of Reproduction 66: 354-360 (2002).
Arav, A et al., New trends in gamete's cryopreservation, Molecular and Cellular Endocrinology 187:77-81 (2002).
Arndt-Jovin et al., "Analysis and Sorting of Living Cells According to Deoxyribonucleic Acid Content", Journal Histochem. and Cytochem., 1977, vol. 25(7), pp. 585-589.
Arts,E.et al.,Evidence for the existence of lipid-diffusion barriers in the equatorial segment of human spermatozoa, Boichem J.384:211-218 (1994).
Gadella B,et al., Dynamics in the membrain organization of the mammalian sperm cell and functionality in fertilization, Vet Quart. 21:142-146 (1999).
Garner,D. et al., Morphological and ultrastrutural Characterization of mammalian spermatozoa processed for flow cytometric DNA analyses, Gamete Research 10:339-351 (1984).
Garner, D., et al., Effect of hoechst 33342 staining and laser illumination on the viability of sex-sorted bovine sperm, Theriogenology, vol. 57 No. 1, 1-810 (2002).
Garner, D., et al., Assessment of spermatozoal function using dual fluorescent staining and flow cytometric analyses, Biology of Reproduction 34:, 127-138 (1986).
Gebhard D., Sorting Viability . . . one more time, http://www.cyto.purdue.edu/hmarchiv/1998/2263.htm Feb. 14, 2004.
Gledhill, B.et al., Identifying and separating X- and Y- Chromosome-bearing mammalian sperm by flow cytometry, Lawrence Livermore National Laboratory, Feb. 8, 1984.
Gledhill, B.et al., Flow microflurometric analysis of sperm DNA contemt: Effect of cell shape on the fluorescence distribution, J. Cell Physiol.87: 367-378.
Gledhill, B.et al., Flow cytometry and sorting of sperm and male germ cells, Flow Cytometry and sorting, second edition, pp. 531-551 (1990).

(56) References Cited

OTHER PUBLICATIONS

Gordon et al.,"Genetic Transformation of Mouse Embryos by Microinjection of Purified DNA", Proc. Natil Acad. Sci., 1980, vol. 77 (12), pp. 7380-7384.
Graham, J.et al.,Analysis of sperm cell viability, Acrosomal integrity, and Mitocondrial function using flow cytometry, Biology of Reproduction 43: 55-64 (1990).
Graham, J.et al., Effect of some Zwitter Ion buffers on freezing and storage of spermatozoa I, Bull, J. Dairy Sci 55: 372-378 ( 1992).
Grogan, W. et al., DNA Analysis and sorting of viable mouse testis cells, The Journal of Histochemistry and Cytochemistry, vol. 29 No. 6 pp. 738-746, (1981).
Guthrie, et al., "Flow Cytometric Sperm Sorting: Effects of Varying laser Power on Embryo Development in Swine", Mol. Reprod. and Develop., 2002,vol. 61 (1), pp. 87-92.
Hacker-Klom, U.B., et al., Effect of doxorubicin and 4'-epidoxorubicin on mouse spermatogenesis. Mutation Research International Journal on Mutagenesis vol. 159, pp. 39-46. 1986.
Hasler, J., Symposium: Reproductive Technology and Genetic improvementJ. Dairy Sci. 75:2857-2879 (1992).
Held, A.et al., Quasi—CW Solid-state lasers Expand their reach, Photonics Spectra, Dec. 2002.
Hinkley, R.et al., Rapid visual detection of sperm-egg fusion using the DNA-Specific Fluorochrome Hoechst 33342, Developmental Biology 118: 148-154 (1986).
Januskauskas, A.et al.,Assessment of sperm quality through Fluorometry and sperm chromatin structure assay in relation to field fertility of frozen-thawed semen from Swedish AI bulls, Theriogenology 55: 947-961 (2001).
Johnson, L., Flow sorting of intact X & Y chromosome-bearingmammalian spermatozoa, The Journal of the Society for Analytical Cytology Cytometry, (1988).
Zhang,M. et al., Development of bovine embryos after in vitro fertilzation of oocytes with a flow cytometrically sorted, stained and unsorted sperm from different bulls, Theriogenology 60: 1657-1663 (2003).
Jones,R.et al., Effect of Osmolality and Phosphate, "Tris", "Tes", "Mes", nd "Herpes" Hydrogen ion buffers on the motility of bull spermatozoa stored at 37 or 5oC, Ausi J. Biol. Sci.25:1047-1055 (1972).
Johnson, L., Prograss towards achieving sex preselection in farm animals, USDA Agricultural Research Service, (1989).
Keeler, K.et al., Flow microfluorometric analysis of living spermatozoa stained with Hoechst 33342, J. Reprod.Fert. 68:205-212 (1983).
Keij, J.et al., High speed Photodamage cell sorting: An evaluation of the Zapper Prototype, Methods in cell Biology vol. 42, (1994).
Kirchhoff, C.et al., The Molecular biology of the sperm surface:Post-Testicular Membrane Remodelling, The Fate of the Male Germ Cell, (1997).
Krueger, C.et al.,Low dose Insemination in synchronized gilts, Theriogenology 52: 1363-1373 (1999).
Lahdetie,J.,Induction and survival of micronuclei in rat spermatids. Comparison of two meiotic micronucleus techniques using cyclophosphamide, Mutation Research, 203:47-53 (1988).
Laser Innovations—Applications, http://www.laserinnovations.com/488nm.htm Feb. 2, 2004.
Libbus, B.et al.,Incidence of chromosome aberrations in mammalian sperm stained with Hoechst 33342 and UV-laser irradiated during flow sorting, Mutation Research, 182: 265-274 (1987).
Loken, M., Separation of viable T and B lymphocytes using a cytochemical stain, Hoechst 33342, The Journal of Histochemistry and Cytochemistry,vol. 28, No. 1, pp. 36-39 (1980).
Lucas, J.et al., Orientation measurments of microsphere doublets and metaphase chromosomes in flow, Cytometry 7:575-581 (1986).
Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Maxwell, W.et al.,Physiology of spermatozoa at high dilution rates:The influence of seminal plasma, Theriogenology 52: 1353-1362 (1999).
Mazur, P., The role of Intracellular freezing in the death of cells cooled at supraoptimal rates, Cryobiology 14:251-272 (1977).
McSweeney,K.et al., Abstract: Insemination of lactating holstein cows with sexed frozen/thawed sperm, http://www.cvmbs.colostate.edu/physio/abstract/ges12.html Mar. 16, 2004.
Medeiros,C. et al., Current status of sperm cryopreservation: Why isn't it better? Theriogenology 57: 327-344 (2002).
Meistrich, M.et al., "Cytogenetic" studies of spermatids of mice carrying Cattanach's translocation by flow cytometry, Chromosoma 74:141-151 (1979).
Morrell, J. et al., Offspring from inseminations with mammalian sperm stained with Hoechst 33342, either with or without flow cytometry, Mutation Research 224:177-183 (1989).
Morrell et al.,"Sexing of Sperm by Flow Cytometry", The Veterinary Record, 1988, pp. 322-324.
Morrier, A.et al., Glycerol addition and conservation of fresh and crypreserved ram spermatozoa, Canadian Journal of AnimalScience, 9/2002http://pubs.nrc-cnrc.gc.ca/aic-journals/2002ab/cjas02/sep02/cjas01-045.html.
Moruzzi, J., Selecting a mammalian species for the separationof X- and Y-chromosome-bearing spermatozoa, J. Reprod. Fert. 57:319-323 (1979).
Studt, T., MEMS-based Cell Sorter Speeds Clinical Studies, R& D Magazine, Dec. 2003: pp. 36-37 as currently presented on and printed from http;//www.rdmag.com 2 pgs.
Gwo-Bin, L.et al., Multi-cell-line micro flow cytometers with buried SU-8/SOG Optical waveguides, Feb. 2002.
Shapiro, H. M. et al., Multistation Multparameter Flow Cytometry: Some Influences of Instrumental Factors on System Performance, 1983,pp. 11-19,4,Allan R. Liss, Inc.
OcanaQuero, J.et al., Biological effects of helium-neon irradiation on acrosome reaction in bull, Scisearch Journal of Photochemistry and Photobiology, vol. 40 No. 3, pp. 294-298 (1997).
Pangawkar, G. et al., Physical and biochemical characteristics of semen in relation to fertility of Holstein-Friesian bulls, Indian vet. Med.J. vol. 13: 21-26 (1989).
Papa, S. et al., Chromatin organization in Isolated nuclei: Flow cytometric characterization employing forward and perpendicular light scatter, Cell Biochemistry and Function vol. 6: 31-38 (1988).
Parks, J. et al., Lipids of plasma membrane and outer acrosomal membrane from bovine spermatozoa, Biology of Reproduction 37:1249-258 (1987).
Partec, Taking flow cytometry to the next generation, Catalogue 2001-2002.
Perez-Pe, R.et al., Semen plasma proteins prevent cold shock membrane damage to ram spermatozoa, Theriogenology 56 (3): 425-434, Aug. 1, 2001, PMID: 11516122 http.//www.ncbi.nlm.nih.gov/entrez/query.fcgi?CMD=search&DB=pubmed.
Peter, A. et al., Fractionation of bovine spermatozoa for sex selection: A rapid immunomagnetic technique to remove spermatozoa that contain the H-Y antigen, Theriogenology 40:1177-1185 (1993).
Petersen, Timothy W., et al., Stability of the Breakoff Point in a High-Speed Cell Sorter The Journal of the international society for Analytical Cytology, vol. 56A No. 2, Dec. 2003.
Pinkel Dan, Flow Cytometry and Sorting Analytical Chemistry, Mar. 1982 vol. 54 No. 3.
Pinkel Dan, Cytometric Analysis of Mammalian Sperm for Induced Morphologic and DNA Content Errors; Biological Dosimetry (Cytometric Approaches to Mammalian Systems) 1984.
Pinkel, D. et al.; Radiation-Induced DNA Content Variability in Mouse Sperm. Radiation Research An International Journal, vol. 95, No. 3, Sep. 1983.
Piumi, F. et al., Specific cytogenetic labeling of bovine spermatozoa bearing X or Y chromosomes using florescent in situ hybridization (FISH), Genet, Sel. vol. 33: 89-98 (2001).
Edited by Bell-Prince, C., NFCR Newsletter, http://www.ls.lanl.gov/NFCR/newsletter-Oc98/oct98.html Jan. 6, 2004.

(56) References Cited

OTHER PUBLICATIONS

Rasul, Z.et al., Changes in motion characteristics, plasma membrane integrity, and acrosome morphology during cryopreservation of buffalo spermatozoa, Journal of Andrology, vol. 22 No. 2, Mar. 4, 2001.
Rees, William A., et al.,Betaine Can Eliminate the Base Pair Composition Dependence of DNA Melting; Biochemistry 1993, 32, pp. 137-144.
Rens, W.et al.,An X-Y paint set and sperm FISH protocol that can be used for validation of cattle sperm separation procedures, Journals of Reproduction and Fertility, 121: 541-546 (2001).
Reyes-Mereno, C.et al., Characterization of Secretory Proteins from cultured Cauda Epididymal Cells that significantly sustain bovine sperm motility, Molecular Reproduction and Development 63: 500-509 (2002).
Rippel,N.et al., Transcervical insemination: Effects of variation in total sperm number/dose on fertility, 83rd Annual Fall Conference for Veterinarians, Oct. 2002.
Rizzo, W. et al.,Liposome-mediated transfer of simian virus 40 DNA and minichromosome into mammalian cells, J. Gen. Virol 64:911-919 (1983).
Ruch, F., Determination of DNA content by microfluorometry, Introduction to Quanitative Cytochemistry, pp. 281-294 (1966).
Salisbury, G.W., et al."Preservation of Bovine Spermatozoa in Yolk-Citrate Diluent and Field Results from its Use", Journal of Dairy Science, 1941, vol. 24(11),pp. 905-910.
Schroter, S.et al., The glycocalyx of the sperm surface, Human Reproduction Update: vol. 5, No. 4, pp. 302-313 (1999).
Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.
Seidel, George E. Jr. "What about sexed semen?" Hoard's Dairyman, The National Dairy Farm Magazine, May 10, 2001.
Sexing Technologies, Welcome to sexing Technologies, http://www.sexingtechnologies.com/ Dec. 11, 2003.
Sharpe, J. et al., Radially symmetric excitation and collection optics for flow cytometric sorting of aspherical cells, Cytometry, 29:363-370 (1997).
Shapiro, H., Re: cheap laser idea??, http://www.cyto.purdue.edu/hmarchiv/1998/1015.htm Feb. 3, 2004.
Smith, P. et al., Characteristics of a Novel Deep Red/ Infrared Fluorescent Cell—Permeant DNA Probe, DRAQ5, in Intact human Cells Analyzed by Flow Cytometry, Confocal and Multiphoton Microscopy, Cytometry 40:280-291 (2000).
Stanger, J.et al. The Relationship between motility and the FITC-BSA binding Properties of Mouse epididymal spermatozoa, The Journal of Experimental Zoology 227: 323-327 (1983).
Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.
Stewart,R., Georgia Beef Challenge, Livestock Newsletter Jan.-Feb. 2002.
Takacs, T.et al.,Flow Cytometric determination of the sperm cell number in diluted bull semen samples by DNA staining method, Acta Biochim.Biophys.Hung. vol. 22 No. 1, pp. 45-57 (1987).
Thurston,L. et al., Identification of Amplified restriction fragment length polymorphism markers linked to genes controlling boar sperm viability following cryopreservation, Biology of Reproduction 66: 545-554 (2002).
Tubman,L.et al., Abstract:Normality of calves resulting from sexed sperm, http://www.cvmbs.colostate.edu/bms/abstract/ges12.html Mar. 16, 2004.
Tucker,K.et al., Sperm separation techniques:Comparison of gradient products, Proceedings 2ed International workshop for Embryologists: Troubleshooting activities in the ART lab. (2002).
Van Dilla, M.et al., Measurement of Mammalian Sperm Deoxyribonucleic acid by Flow Cytometry, The journal of Histochemistry and Cytochemistry vol. 25 No. 7 pp. 763-773 (1977).
Vazquez, J.et al., Nonsurgical Uterotubal Insemination in the Mare, Reproduction: Mare vol. 44 (1998).
Vishwanath,R.et al., Storage of bovine semen in liquid and frozen state, Animal Reproduction Science 62: 23-53 (2000).
Washburn, S., Sex-Sorted Semen; Still several steps short of sensational, http://www.cals.ncsu.edu/an sci/extention/animal/news/april96/april1965.html Mar. 16, 2004.
Welch,G.et al., Sex preselection: Laboratory Validation of the sperm sex ratio of Flow sorted X- and Y-sperm by sort reanal ysis for DNA, Theriogenology 52:1343-1352 (1999).
Welch, G.et al., Fluidic and optical modification to a facs IV for flow sorting of X&Y Chromosomes bearing sperm based on DNA, International Society for Analytical Cytology (1994).
Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).
Woelders, H. et al., Effects of Trehalose and Sucrose, Osmolality oh the freezing medium, and cooling Rate on Viability and intactness of bull sperm after freezing and thawing, Cryobiology 35: 93-105 (1997).
Wolf, D., Lipid domains in sperm plasma membranes, Molecular Membrane Biology 12: 101-104 (1995).
Wolf, D.et al., Changes in sperm plasma membrane lipid diffusibility after hyperactivation during In vitro capacitation in the mouse, The Journal of Cell Biology, vol. 102: 1372-1377(1986).
Wolf, D.et al., Diffusion and regionalization in membranes of maturing ram spermatozoa,The Journal of Cell Biology, vol. 98:1678-1684 (1984).
XY Files, Issue 1 Jun. 1999.
X Y, Inc., Sex selection Procedure, http://www.xyinc.com/sex select. html, Feb. 21, 2003.
XY Files, Issue 4 Aug. 2000.
XY Files, Issue 2 Oct. 1999.
XY Files, Issue 3 Mar. 2000.
XY Files, Issue 5 Mar. 2001.
XY Files, Issue 6 Mar. 2002.
Lindsey, A. C., et al., Hysteroscopic inseminatin of mares with low numbers of nonsorted or flow sorted spermatozoa; Equine vet. J. (2002) 34(2) 128-132.
Parallel Australian Patent Application No. 2003277099; Office Action dated Jan. 11, 2008.
Parallel Chinese Patent Application No. 03821753.8; Office Action dated Sep. 1, 2006.
Parallel European Patent Application No. 03795716.4; Office Action dated Mar. 5, 2008.
Parallel New Zealand Patent Application No. 539388; Office Action dated Apr. 27, 2006.
Parallel New Zealand Patent Application No. 539388; Office Action dated Jan. 10, 2008.
Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.
Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P et al., "Issues Affecting Commercialization of Sexed Sperm" Therio. 52:1441. (1999).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).

(56) References Cited

OTHER PUBLICATIONS

Anderson, V. K., et al., Intrauterine und tiefzervikale Insemination mit Gefriersperma bein Schat (Intrauterine and Deep Cervical Insemination with Frozen Semen in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterone Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., et al., 1999 Sexual Dimorphism In IVM-IVF Bovine Embryos Produced from X and Y Chromosome-Bearing Spermatozoa Sorted By High Speed Flow Cytometry. Theriogenology. 52:35-48.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sd. 65:963. 1987.
Braselton, W. E. and McShan, W. H., "Purification and Properties of Follicle Stimulating and Luteinizing Hormones From Horse Pituitary Glands" Arch. Biochem. Biophys. 139:45-48.1970.
Braun, J. et al., "Effect of Different Protein Supplements on Motility and Plasma Membrane Integrity of Frozen—Thawed Stallion Spermatozoa", Cryobiology (1995) 32:487-492.
Brethour, J. R. and Jaeger, J. R., "The Single Calf Heifer System", Kansas Agric. Sta. Rep of Progress 570. 1989.
Brinsko, S.P. et al., "Artificial Insemination and Preservation of Semen." Veterinary Clinics of North America:Equine Practice vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byme, M., "Use of Cow-Heifers in Beef Production" J. of the Royal Agriculture Society of England 126:30. 1965.
Buchanan, B. R., et al., "Insemination of Mares with Low Numbers of Either Unsexed or Sexed Spermatozoa", Therio. vol. 53, p. 1333-1344. 2000.
Burns, P. D. and Spitzer, J.C., "Influence of Biostimulation on Reproduction in Postpartum Beef-Cows", J. Anim. Sci. 70:358. 1992.
Burwash, L. D., et al., "Relationship of Duration of Estrus to Pregnancy Rate in Normally Cycling, Non Lactating Mares" J.A.V.M.A. 165:714-716. 1974.
Byerley, D. J., et al., "Pregnancy Rates of Beef Heifers Bred Either on Puberal or Third Estrus". J Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, et al., "Assessment of Ram and Boar Spermatozoa During Cell-Sorting by Flow Cytometry", Reproduction Dom Animal, vol. 32, pp. 251-258. 1997.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.
Cave-Penney, Tony, "Sexed Semen Offers Faster Genetic Gain", Farming News, Livestock Supplement, Feb. 1997, p. 28.
Chandler, J. E., "Videomicroscopic Comparison of Bull Sperm and Leukocyte Chromosome Areas as Related to Gender", J Dairy Sci 73, p. 2129-2135. 1990.
Chandler, J. E., et al., "Bovine Spermatozoal Head Size Variation and Evaluation of a Separation Technique Based on this Size", Therio. 52, p. 1021-1034. 1999.
Chen, S.H. "Effects of Oocyte Activation and Treatment of Spermatozoa on Embryonic Development Following Intracytoplasmic Sperm Injection in Cattle" Theriogenology 48: 1265-1273, 1997.
Chen, Y. et al., Survival of Bull Spermatozoa Seeded and Frozen at Different Rates in Egg Yolk-Tris and Whole Milk Extenders, 1993 J Dairy Sci 76:1028-1034.
Chin, W. W. and Bolme, I. 1990. In Glycoprotein Hormones. Serona Symp. Norwell, MA. pp. 19-20.
Choi, Y.H. "Developmental Cappacity of Equine Oocytes Matured and Cultured in Equine Trophoblast-Conditioned Media" Theriogenoogy 56:320-339, 2001.
Chung, Y. G., et al. "Artificial insemination of Superovulated Heifers With 600,000 Sexed Sperm". J Anim. Sci. Suppl. 1. 836:215. 1998 abstr.
Clement, F., et al., "Which Insemination Fertilizes When Several Successive Inseminations are Performed Before Ovulation" 7th Int. Symp. Eq. Repro. 151. 1998 abstr.
Cran, D. G., et al., "Sex Preselected in Cattle: A Field Trial", Veterinary Record 136, 1995, p. 495-496.
Cran, D. G., et al., "Production of Bovine Calves Following Separation of X- and Y-Chromosome Bearing Sperm and In Vitro Fertilization". Vet. Rec. 132:40-41. 1993.
Cran, D. G., et al., "The Predetermination of Embryonic Sex Using Flow Cytometrically Separated X and Y Spermatozoa" Human Reproduction Update 1996, vol. 2 (4) p. 355-63.
Cui, K. et al., "X Larger than Y", Nature 366, p. 177-118, 1993.
Cui, K., "Size Differences Between Human X and Y Spermatozoa and Prefertilization Diagnosis", Molecular Human Reproduction, vol. 3, No. 1, pp. 61-67. 1997.
Curran, S. "Fetal Gender Determination" in *Equine Diagnostic Ultrasonography* 1st ed. Rantanen, N.W. and McKinnon A.O. (eds.) Williamsand Williams, 1998, p. 165-69.
Da Silva, Coutinho M.A.."Effect of time of oocyte collection and site of Insemination on oocyte transfer in mares." Animal Reproduction and Biotechnology Labotatiory, Colorado State Uniuversity, Fort Collins Journal of Animal Science 2002. 80:1275-1279.

(56) References Cited

OTHER PUBLICATIONS

DakoCytomation. "MoFlo® Sorters"http://www.dakocytornation. us/prod_productrelatedinformation?url=gprod_moflo_index.htm one Page, printed Jun. 26, 2003.
Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.
De Leeuw, F.E. et al.:"Effects of carious cryoprotective agents and membrane-stabilizing compounds on bull sperm emebrane integrity after cooling and freezing" Cryobiology US, Academic Press Inc 1993 pp. 32-44.
Dean, P.N., et al. "Hydrodynamic Orientation of Spermatozoa Heads for Flow Cytometry". Biophys. J. 23:7-13.1978.
Demick, D.S., et al. "Effect of Cooling, Storage, Glycerization and Spermatozoal Numbers on Equine Fertility" J. Anim. Sci. 43:633-637. 1976.
DenDaas, J. H. G., et al. "The relationship between the number of spermatozoa inseminated and the reproductive efficiency of dairy bulls" J Dairy Sci. 81: 1714-1723. 1998.
Deutscher, G. H. "Extending Interval From Seventeen to Nineteen Days in the Melengestrol Acetate-Prostaglandin Estrous Synchronization Program for Heifers". The Professional Animal Scientist 16:164. 2000.
*Diacnostic Products Corporation*, "Coat-A-Count" http://www. Progesterone.com. 1998.
Dikeman, M. E. "Cattle Production Systems to Meet Future Consumer Demands" J. Anim. Sci. 59:1631, 1984.
Dinnyes, A., et al., "Timing of the First Cleavage Post—Insemination Affects Cryosurvival of In Vitro-produced Bovine Blastocysts", Molec. Reprod. Develop. 53, p. 318-324. 1999.
Dippert, K.D. "Fertilization Rates in Superovulated and Spontaneously Ovulating Mares" Theriogenology 41: 1411-1423, 1994.
Donaldson, L. E., "Effect of Insemination Regimen on Embryo Production in Superovulated Cows", The Veterinary Record, Jul. 13, p. 35-37, 1985.
Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.
Douglas, R. H., "Review of Induction of Superovulation and Embryo Transfer in the Equine" Therio. 11:33-46. 1979.
Douglas, R. H., et al. "Induction of Ovulation and Multiple Ovulation on Seasonally-Anovulatory Mares with Equine Pituitary Fractions." Therio. 2(6): 133-142. 1974.
Doyle, S. P., et al. "Artificial Insemination of Lactating Angus Cows with Sexed Semen". Proc. Western Sect. Am. Soc. Anim. Sci. 50:203. 1999.
Dresser D.W. et at. Analysis of DNAcontent ofLiving Spermatozoa Using Flow Cytometry Technique Journal of Reproduction and Fertility, 1993, vol. 98, pp. 357-365.
Duchamp, G., et al. "Alternative Solutions to hCG Induction of Ovulation in the Mare" J. Reprod. Fertil. Suppl. 35:221-228. 1987.
Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.
Ferrell, C. L. Effects of Post-Weaning Rate of Gain on Onset of Puberty and Productive Performance of Heifers of Different Breeds. J. Anim, Sci. 55:1272. 1982.
Ferrell, C. L. and T. G. Jenkins. "Energy-Utilization by Mature, Nonpregnant, Nonlactating Cows of Different Types" J. Anim. Sci. 58:234. 1984.
Field, R. A., et al., "Bone-Ossification and Carcass Characteristics of Wethers Given Silastic Implants Containing Estradiol", J. Anim. Sci. 68:3663-3668. 1990.
Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.
Fluharty, F. L., et al., "Effects of Age at Weaning and Diet on Growth of Calves",Ohio State University Dept. of Animal Scieneces. 1966 Ohio Agri. Res. and Den. Circular, 156:29 1966.
Foote, et al. Motility and Fertility of Bull Sperm Frozen-Thawed Differently in Egg Yolk and Milk Extenders Containing Detergent, 1987 J Dairy Sci 70:2642-2647.
Foote, R.H., "Buffers and Extenders: What Do They Do? Why Are They Important?" Proc of the NAAB Tech. Conf. on Artificial Insemination and Reproduction, 62-70 (1984).
Foulkes, J. A., et al. "Artificial Insemination of Cattle Using Varying Numbers of Spermatozoa." Vet. Rec. 101:205. 1977.
Francon, M. and Yamamoto, T., "Un Noveau et tres simple dispositif interferential applicable as microscope" Optica Acta 9, p. 395-408. 1962.
Fugger, E. F. "Clinical Experience with Flow Cytometric Separation of Human X- and Y-Chromosome Bearing Sperm", Therio. vol. 52, pp. 1435-1440. 1999.
Fulwyler, M. J. "Electronic Separation of Biological Cells by Volume." Science. 150:910. 1965.
Fulwyler, M. J. "Hydrodynamic Orientation of Cells." J of Histochem. and Cytochem. 25:781-783. 1977.
Garner, D. L., et al. "Quantification of the X and Y Chromosome-Bearing Spermatozoa of Domestic Animals by Flow Cytometry." Biol. Reprod. 28:312-321. 1983.
Ginther, O. J., "Sexual Behavior Following Introduction of a Stallion into a Group of Mares" Therio. vol. 19 (6) Jun. 1983.
Ginther, O. J., "Some Factors Which Alter Estrus Cycle in Mares." J. Anim. Sci. 33:1158. 1971 abstr.
Ginther, O. J., Reproductive Biology of the Mare. (2nd Ed.) Equiservices, Cross Plains, WI. 1992.
Gledhill, B. L. "Gender Preselection: Historical, Technical and Ethical Perspective." Semen Reprod. Endocrinol. 6:385-395. 1988.
Gombe, S. and Hansel, W. "Plasma Luteinizing☐Hormone (LH) and Progesterone Levels in Heifers on Restricted Energy Intakes." J. Anim. Sci. 37:728. 1973.
Gourley, D. D. and Riese, R. L. "Laparoscopic Artificial Insemination in Sheep." Vet. Clin. N. Amer: Food Anim. Prac. 6(3): 615-633 (1990).
Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).
Graham, James K., "Effect of Cholesterol-Loaded Cyclodextrins in Semen Extenders", Proceedings of the 19th Technical Conference on Artificial Insemination & Reproduction, 2003, pp. 91-95.
Gravert, H. O., "Genetic Aspects of Early Calving." In: J.C. Taylor (Ed.) *The Early Calving of Heifers and Its Impact on Beef Production.* 59 (1975).
Gregory, K. E., et al., "Characterization of Biological Types of Cattle—Cycle III: II Growth Rate and Puberty in Females" J. Anim. Sci. 49:461 (1979).
Grimes, I. F, and T. B, Turner. "Early Weaning of Fall Bom Calves II. Post Weaning Performance of Early and Normal☐Weaned Calves". I. Prod. Agric. 4:168 (1991).
Grondahl, C., et al., "In Vitro Production of Equine Embryos", Biology of Reproduction, Monograph Series I, p. 299-307 (1995).
Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).
Hall, J. B., et al., "Effect of Age and Pattern of Gain on Induction of Puberty with a Progestin in Beef Heifers." J. Anim. Sci. 75:1606 (1997).
Hamamatsu. "*Technical Information. Optical Detector Selection: A Delicate Balancina Act*", web page, http://www.optlcs.org/hamamatsu/ photodiode.html. printed on Apr. 15, 2000, 6 pages total.
Hamano, K., et al., "Gender Preselection in Cattle with Intracytoplasmically Injected, Flow Cytometrically Sorted Sperm Heads", Biology of Reproduction 60, p. 1194-1197 (1999).

(56) References Cited

OTHER PUBLICATIONS

Hammerstedt, et al., "Cryopreservation of Mammalian Sperm: What We Ask Them to Survive," Journal of Andrology, 11:1:73-88 (1990).
Harrison, L.A., et al., "Comparison of HCG, Buserelin and Luprostiol for Induction of Ovulation in Cycling Mares." Eq. Vet. Sci. 3:163-166 (1991).
Hawk, H. W., et al., "Fertilization Rates in Superovulating Cows After Deposition of Semen on the Infundibulum Near the Uterotubal Junction or After Insemination with High Nos. of Sperm", XP-002103478, Therio. Vol. 29, No. 5, p. 1131-1142 (1988).
Hermesmeyer, G. N., et al. "Effects of Prenatal Androgenization and Implantation on the Performance and Carcass Composition of Lactating Heifers in the Single-Calf Heifer System." The Professional Animal Scientist 15:173.1999.
Herweijer, Hans. "High-Speed Photodamage Cell Selection Uing Bromodeoxyuridine/Hoechst 33342 Photosensitized Cell Killing," Sep. 23, 1987.
Hilton, G. G., et al., "An Evaluation of Current and Alternative Systems for Quality Grading Carcasses of Mature Slaughter Cows." J. Anim. Sci. 76:2094.1998.
Ho, L., et al., "Influence of Gender, Breed and Age on Maturity Characteristics of Sheep." J. Anim. | Sci. 67:2460-2470.1989.
Hofferer, S., et al. "Induction of Ovulation and Superovulation in Mares Using Equine LH and FSH Separated by Hydrophobic Interaction Chromatography." J. Reprod. Fertil. 98:597-602. 1993.
Hohenboken, W. D. "Applications of sexed semen in cattle production." Therio. 52:1421.1999.
Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.
Householder, D. D., et al. "Effect of Extender, No. of Spermatozoa and hCG on Equine Fertility." J. Equine Vet. Sci. 1:9-13.1981.
Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118.1991.
Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.
Hunter, R. H. F. "Transport and Storage of Spermatozoa in the Female Tract." Proc 4th Int. Congress Anim. Repro, and A. 1.9:227-233.1980.
Iwazumi, Y., et al., "Superovulation Using CIDR in Holstein Cows" J. of Reprod. Dev. vol. 40 (3) 1994, pp. 259-266.
Jafar, et al., "Sex Selection in Mammals: A Review", Therio. vol. 46, p. 191-200. (1996).
Jakubiczka, S et al. "A Bovine Homologue of the Human TSPY Gene." Genomics. 1993, vol. 17, No. 3, pp. 732-735.
Jasko, D. J., et al., "Effect of Insemination Volume and Concentration of Spermatozoa on Embryo Recovery in Mares", Therio. 37:1233-1239, (1992).
Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.
Johnson, A. L. "Pulsatile Administration of Gonadotropin Releasing Hormone Advances Ovulation in Cycling Mares", Biol. Reprod. 35:1123-1130, (1986).
Johnson, A. L., et al. "Use of Gonadotropin-Releasing Hormone (GnRH) Treatment to Induce Multiple Ovulations in the Anestrous Mare" Eq. Vet. Sci. 8:130-134, (1988).
Johnson, L.A., "Gender Preselection in Domestic Animals Using Flow Cytometrically Sorted Sperm" J. Anim. Sci. (Suppl I) 70:8-18. (1992).
Johnson, L.A., "The Safety of Sperm Selection by Flow Cytometry" Ham. Reprod. 9(5): 758. (1994).
Johnson, L.A., "Advances in Gender Preselection in Swine" Journal of Reproduction and Fertility Supplement, vol. 52, p. 255-266 (1997).
Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).
Johnson, L.A., "Gender Preselection in Mammals: An Overview", Deutsch. Tierarztl. Wschr, vol. 103, p. 288-291 (1996).
Johnson, L.A., "Isolation of X- and Y-Bearing Spermatozoa for Sex Preselection." Oxford Reviews of Reproductive Biology. Ed. H. H. Charlton. Oxford University Press. 303-326. (1994).
Johnson, L.A., "Sex Preselection by Flow Cytometric Separation of X and Y Chromosome Bearing Spermatozoa Based on DNA Difference: a Review." Reprod. Fertil. Dev. 7:893-903. (1995).
Johnson, L.A., "Sex Preselection in Rabbits: Live Births from X and Y Sperm Separated by DNA and Cell Sorting", Biology of Reproduction 41, pp. 199-203 (1989).
Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).
Johnson, L.A., et al. "Sex Preselection: High-speed Flow Cytometric Sorting of X and Y Sperm for Maximum Efficiency", Therio. vol. 52, p. 1323-1341 (1999).
Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.
Johnson, L.A., et al., "Flow Sorting of X and Y Chromosome-Bearing Spermatozoa into Two Populations", Gamete Res. 16:203-212. (1987).
Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).
Johnson, L.A., et al., "Flow Cytometry of X- and Y-Chromosome Bearing Sperm for DNA Using an Improved Preparation Method and Staining with Hoechst 33342." Gamete Research 17:203-212. (1987).
Johnson, L.A., et al., "Modification of a Laser-Based Flow Cytometer for High-Resolution DNA Analysis of Mammalian Spermatozoa" Cytometry 7, pp. 268-273 (1986).
Joseph, R. L. and J. P. Crowley. "Meat Quality of Once-Calved Heifers." Irish J. of Agric. Research 10:281. (1971).
Kachel, V., et al., "Uniform Lateral Orientation, Caused by Flow Forces, of Flat Particles in Flow-Through Systems", The Journal of Histochemistry and Cytochemistry, vol. 25. No. 7, pp. 774-780. (1997).
Kanayama, K., et al., "Pregnancy by Means of Tubal Insemination and Subsequent Spontaneous Pregnancy in Rabbits." J. Int. Med. Res. 20:401-405. (1992).
Karabinus, et al., "Effects of Egg Yolk-Cltrate and Milk Extenders on Chromatin Structured Viability of Cryopreserved Bull Sperm", Journal of Dairy Science, vol. 74, No. 11, p. 3836-3848. (1999).
Keeling, P. "A Modeling Study of Once-Bred Heifer Beef Production." Proceedings of the New Zealand Society of Animal Production. 51. (1991).
Kilicarslan, M. R., et al., "Effect of GnRH and hCG on Ovulation and Pregnancy in Mares." Vet. Rec. 139:119-120. (1996).
Kinder, J. E., et al., "Endocrine Regulation of Puberty in Cows and Ewes." J. Repro. and Fertility, Suppl. 34:167. (1987).
Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).
Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).
Kniffen, D. M., et al., "Effects of Long-Term Estrogen Implants in Beef Heifers." J. Anim. Sci. 77:2886. (1999).
Kobata, Akira, "Structures and Functions of the Sugar Chains of Human Chorionic Gonadotropin", in *Glycoprotein Hormones* Chin. W.W. and Boime, I., eds. Serono Symposia, Norwell, MA. p. 19-20. 1990.

(56) References Cited

OTHER PUBLICATIONS

Koch, R. M., et al., "Characterization of Biological Types of Cattle—Cycle-II .3." Carcass Composition, Quality and Palatability. J. Anim. Sci. 49:448. (1919).
Kommisrud E., et al. "Comparison of Two Processing Systems for Bull Semen with Regard to Post-Thaw Motility and Nonreturn Rates." Theriogenology, vol. 45, 1996, pp. 1515-1521.
Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).
Laster, D. B., "Factors Affecting Dystocia and Effects of Dystocia on Subsequent Reproduction in Beef-Cattle." J. Anim. Sci. 36:695. (1973).
Lawrenz, R. "Preliminary Results of Non-Surgical Intrauterine Insemination of Sheep With Thawed Frozen Semen." J S Afr. Vet. Assoc. 56(2): 61-63. (1985).
Levinson, G., et al., "DNA-based X-Enriched Sperm Separation as an Adjunct to Preimplantation Genetic Testing for the Preparation of X-linked Disease." Mol. Human Reprod. 10:979-982. (1995).
Lindsey, A. C., et al., "Low Dose Insemination of Mares Using Non-Sorted and Sex-Sorted Sperm" Animal Reproduction Science 68 p. 279-89 (2001).
Linge, F. "Faltforsok med djupfrost sperma (Field Trials With Frozen Sperm)." Farskotsel. 52:12-13. (1972).
Liu, Z, et al. "Survival of Bull Sperm Frozen at Different rates in Media Varying in Osmolarity." Cryobiology, vol. 27, 1998, pp. 219-230.
Lonergan, P., et al., "Effect of Time Interval from Insemination to First Cleavage on the Development of Bovine Embryos In Vitro and In Vivo", Therio. p. 326 (1999).
Long, C.R., et al., "In Vitro Production of Porcine Embryos From Semen Sorted for Sex With a High Speed Cell Sorter: Comparison of Two Fertilization Media." Therio. 49(1): 363 (1998) abstr.
Loy, R. G. and Hughes, J.P. "The Effects of Human Chorionic Gonadotropin on Ovulation, Length of Estrus, and Fertility in the Mare." Cornell Vet. 56:41-50 (1965).
Lu, K. H., et al., "In Vitro Fertilization with Flow-Cytometrically-Sorted Bovine Sperm", Therio 52, p. 1393-1405. (1999).
Lynch, I. M., et al., "Influence of timing of gain on growth and reproductive performance of beef replacement heifers." J. Anim. Sci. 75:1715. (1997).
Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).
Martin, A. H., et al., "Characteristics of Youthful Beef Carcasses in Relation to Weight, Age and Sex. III. Meat Quality Attributes." Canadian J. Anim. Sci. 51:305. (1971).
Martin, L. C., et al., "Genetic-effects on Beef Heifer Puberty and Subsequent Reproduction." J. Anim. Sci. 70:4006. (1992).
Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).
Matulis, R. J., "Growth and carcass characteristics of cull cows after different times-on-feed." J. Anim. Sci. 65:669. (1987).
Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).
Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).
Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).
McCormick, R. J. "The Flexibility of the Collagen Compartment of Muscle." Meat Sci. 36:79. (1994).
McCue, P.M. "Superovulation" Vet. Clin. N. Amer. Eq. Prac. 12:1-11. (1996).
McCue, P.M., et al.,, "Oviductal insemination in the mare." 7th Internat. Symp. Eq. Reprod. 133 (1997) abstr.
McDonald, L. E. "Hormones of the Pituitary Gland." Veterinary Pharmacology and Therapeutics. 6th ed. Edited by N. H. Booth and L. E. McDonald. Ames, Iowa State Univ. Press, p. 590 (1988).
McKenna, T. et al., "Nonreturn Rates of Dairy Cattle Following Uterine Body or Cornual Insemination." J. Dairy Sci. 73:1179-1783 (1990).
McKinnon, A.O. and Voss, J. L. Equine Reproduction. Lea and Febiger. Philadelphia, London (1993).
McKinnon, A.O., et al., "Predictable Ovulation in Mares Treated With an Implant of the GnRH Analogue Deslorelin." Eq. Vet. J. 25:321-323. (1993).
McKinnon, A.O., et al., "Repeated Use of a GnRH Analogue Deslorelin (Ovuplant) for Hastening Ovulation in the Transitional Mare." Eq. Vet. J. 29:153-155. (1996).
McLeod, John H., "The Axicon: A New type of Optical Element", Journal of the Optical Society of America, vol. 44 No. 8, Aug. 1954, Eastman Kodak Company, Hawk-Eye Works, Rochester, New York.
McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).
Meilgaard, M., et al., "Sensor Evaluation Techniques." CRC Press Inc., Boca Raton, FL. (1991).
Meinert, C., et al., "Advancing the Time of Ovulation in the Mare With a Short-Term Implant Releasing the GnRH Analogue Deslorelin", Equine Veterinary Journal, 25, p. 65-68 (1993).
Mendes Jr., J.O.B. "Effect of heparin on cleavage rates and embryo production with four bovine sperm prepration protocols" Theriogenology (2003) 331-340.
Menke,E. A Volume Activated Cell Sorter Journal of Histo chemistry and Cyto Chemistry, 1977, vol. 25,No. 7, pp. 796-803.
Merton, J., et al., "Effect of Flow Cytometrically Sorted Frozen/Thawed Semen on Success Rate of In Vitro Bovine Embryo Production", Therio. 47, p. 295. (1997).
Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991 vol. 30 pp. 250-257.
Meyers, P. J., et al., "Use of the GnRH Analogue, Deslorelin Acetate, in a Slow Release Implant to Accelerate Ovulation in Oestrous Mares." Vet. Rec. 140:249-252. (1997).
Michaels, C., "Beef A. I. Facilities That Work", Proc. Fifth N.A.A.B Tech, Conf. A. I. Reprod. Columbia, MO. pp. 20-22.
Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).
Miller, S. J. "Artificial Breeding Techniques in Sheep." Morrow, D.A. (ed): Current Therapy in Therio 2, Philadelphia, WB Saunders. (1986).
Mirskaja, L. M. and Petropavloskii, V.V. "The Reduction of Normal Duration of Heat in the Mare by the Administration of Prolan." Probl. Zivotn. Anlm. Breed. Abstr. 5:387. (1937).
Molinia, F. C., et al., "Successful Fertilization After Superovulation and Laparoscopic Intrauterine Insemination of the Brushtail Possum Trichosurus vulpecula, and Tammar Wallaby, Macropus eugenii." J. Reprod. Fertil. 112:9-17. (1998).
Moran, C., et al., "Puberty in Heifers—a Review." Animal Reproduction Sci. 18:167. (1989).
Moran, D. M. et al., "Determination of Temperature and Cooling Rate Which Induce Cold Shock in Stallion Spermatozoa", Therio. vol. 38 p. 999-1012 (1992).

(56) References Cited

OTHER PUBLICATIONS

Morcom, C. B. and Dukelow, W.R. "A Research Technique for the Oviductal Insemination of Pigs Using Laparoscopy." Lab. Anim. Sci. p. 1030-1031. (1980).
Morgan, J. B., et al., "National Beef Tenderness Survey." J. Anim. Sci. 69: 3274. (1991).
Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).
Morris, S. T., et al., "Biological efficiency: How relevant is this concept to beef cows in a mixed livestock seasonal pasture supply context?" Proceedings of the New Zealand Society of Animal Production 54:333. (1994).
Moseley, W. M., et al., "Relationship of Growth and Puberty in Beef Heifers Fed Monensin" J. Anim. Sci. vol. 55 No. 2 p. 357-62 (1982).
Muller, W. and Gautier, F. "Interactions of Heteroaromatic Compounds with Nucleic Acids." Euro. J Biochem. 54:358. (1975).
Mullis, K. B. and F. A. Faloona, "Specific Synthesis of DNA in Vitro Via a Polymerase-Catalyzed Chain Reaction" Methods in Enzymology vol. 155 p. 335-350 (1978).
Munne, S. "Flow Cytometry Separation of X and Y Spermatozoa Could be Detrimental to Human Embryos", Hum. Reprod. 9(5): 758 (1994).
Myers, S. E., "Performance and Carcass Traits of Early-Weaned Steens Receiving Either a Pasture Growing Period or a Finishing Diet at Weaning." J. Anim. Sci. 77:311. (1999).
Myers, S. E., et al., "Comparison of Three Weaning Ages on Cow-Calf Performance and Steer Carcass Traits." J. Anim. Sci. 77:323. (1999).
Myers, S. E., et al., "Production Systems Comparing Early Weaning to Normal Weaning With or Without Creep Feeding for Beef Steers." J. Anim. Sci. 77:300. (1999).
Nix, J. P., et al., "Serum Testosterone Concentration, Efficiency of Estrus Detection and Libido Expression in Androgenized Beef Cows." Therio. 49: 1195. (1998).
Nowshari, et al., "Superovulation of Goats with Purified pFSH Supplemented with Defined Amounts of pLH", Therio. vol. 43, p. 797-802 (1995).
NRC. "Nutrient Requirements for Beef Cattle." National Academy of Sci. National Research Council, Washington, DC. (1996).
Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).
Ozhin F.V. et al. Artificial insemination of farm animals. Moscow, Izdatelstvo Selskokhozyaastvennoi Literatury, 1961, pp. 350-361 and pp. 380-393.
Parrish, J. J., et al., "Capacitation of Bovine Sperm by Heparin", Department of Meat and Animal Science, Biology of Reproduction 38, p. 1171-1180 (1988).
Patterson, D. J., et al., "Estrus Synchronization with an Oral Progestogen Prior to Superovulation of Postpartum Beef Cows" Therio. 48, 1025-33 (1997).
Peippo, J., et al., "Sex Diagnosis of Equine PreImplantation Embryos Using the Polymerase Chain Reaction", Therio. vol. 44:619-627 (1995).
Penfold, L.M.et at., "Comparative Motility of X and Y Chromosome-Bearing Bovine Sperm Separated on the Basis of DNA Content", Mol. Reprod. and Develop. 1998, vol. 50,pp. 323-327.
Perry, E. J., "Historical Background" The Artificial Insemination of Farm Animals. 4th ed. E. J. Perry (ed.) New Brunswick, Rutgers University Press, pp. 3-12. (1968).
Petersen, G. A., et al., "Cow and Calf Performance and Economic-Considerations of Early Weaning of Fall-Born Beef Claves", J. Anim. Sci., 64:15, pp. 15-22. (1987).
Petit, M. "Early Calving in Suckling Herds." In: J.C. Taylor (ed.) *The Early Calving of Heifers and its Impact on Beef Production*, p. 157-176. (1975).

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).
Pickett, B. W., et al., "Effect of Seminal Extenders on Equine Fertility." J. Anim. Sci. 40:1136-1143. (1975).
Pickett, B. W., et al., "Influence of Seminal Additives and Packaging Systems on Fertility of Bovine Spermatozoa." J. Anim. Sci. Suppl. II. 47:12. (1978).
Pickett, B. W., et al., "Management of the Mare for Maximum Reproductive Efficiency." CSU Anim. Repro. Lab. Bull. No. 06. Fort Collins CO. (1989).
Pickett, B. W., et al., "Procedures for Preparation, Collection, Evaluation and Insemination of Stallion Semen." CSU Exp. Sta. Artira. Reprod. Lab. Gen. Series Bull. 935. (1973).
Pickett, B. W., et al., "Recent Developments in Artificial Insemination in Horses", Livestock Production Science, 40, p. 31-36 (1994).
Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).
Pinkel, D., et al., "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).
Pinkel, D., et al., "High Resolution DNA Content Measurements of Mammalian Sperm", Cytometry 3:1-9. (1982).
Pinkel, D., et al., "Sex Preselection in Mammals? Separation of Sperm Bearing the Y and "O" Chromosomes in the Vole Microtus Oregoni", Science vol. 218 p. 904 (1982).
Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).
Polge, et al., "Revival of Spermatozoa After Vitrification and Dehydration at Low Temperatures," Nature, 164:666 (1994).
Preza, C. et al., "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).
Prokofiev M.l. Regoulyatsia Razmnozhenia Selskokhozyastvennykh Zhivotnykh, Leningrad, NAOUKA Publishing House, 1983, pp. 181-195.
Province, C.A., et al., Cooling Rates, Storage, Temperatures and Fertility of Extended Equine Spermatozoa Therio. vol. 23 (6) p. 925-934, Jun. 1985.
Pursel, et al., "Effect of Orvus ES Paste on Acrosome Morphology, Motility and Fertilizing Capacity of Frozen-Thawed Boar Sperm," Journal of Animal Science, 47:1:198-202 (1978).
Purvis, H. T. and J. C. Whittier. "Effects of Ionophore Feeding and Anthelmintic Administration on Age and Weight at Puberty in Spring-Born Beef Heifers." J. Anim. Sci. 74:736-744, (1996).
Randel, R. D. "Nutrition and Postpartum Rebreeding in Cattle." J. Anim. Sci. 68:853. (1990).
Rath, D., et al., "Low Dose Insemination Technique in the Pig", Boar Semen Preservation IV, p. 115 118. (2000).
Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).
Rathi, R. et al., "Evaluation of In Vitro Capacitation of Stallion Spermatoza", Biology of Reproduction 2001,vol. 65, pp. 462-470.
Recktenwald, Diether. "Cell Separation Methods and Applications," New York 1997.
Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.
Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

(56) References Cited

OTHER PUBLICATIONS

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).
Rens, W., et al., "Improved Flow Cytometric Sorting of X- and Y-Chromosome Bearing Sperm: Substantial Increase in Yield of Sexed Semen", Molecular Reproduction and Development, p. 50-56(1999).
Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).
Riggs, B.A. "Integration of Early Weaning and Use of Sexed Semen in a Single-Calf Heifer System to Increase Value of Non-Replacement Heifers" MS Thesis, Colorado State University, Spring 2000.
Ritar, A. and Ball, A., "Fertility of Young Cashmere Goats After Laparoscopic Insemination." J. Agr. Sci. 117: p. 271-273. (1991).
Roberts, J. R., Veterinary Obstetrics and Genital Diseases. Ithaca, New York. p. 740-749. (1971).
Romero-Arredondo, A. "Effects of Bovine Folicular Fluid on Maturation of Bovine Oocytes" Theriogenology 41: 383-394, 1994.
Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.
Roser, J. F., et al., "Reproductive Efficiency in Mares With Anti-hCG Antibodies." Proc 9th Int. Congr. Anim. Repro, and A. I. 4:627 (1980) abstr.
Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).
Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).
Rowley, H. S., et al., "Effect of Insemination Volume on Embryo Recovery in Mares." J. Equine Vet. Sci. 10:298-300 (1990).
Roy, J. H., "Rearing Dairy-Herd Replacements." Journal of the Society of Dairy Technology 31:73-79 (1978).
Rutter, L. M., et al., "Effect of Abomasal Infusion of Propionate on the GnRH-lnduced Luteinizing Hormone Release in Prepuberal Heifers." J. Anim. Sci. 56:1167 (1983).
Salamon, S., *Artificial Insemination of Sheep*, Chippendale, New South Whales. Publicity Press p. 83-84 (1976).
Salisbury, G. W. and VanDemark, N. L. "Physiology of Reproduction and Artificial Insemination of Cattle." San Francisco: Freeman and Company, p. 442-551 (1978) (1961 & 1978 Combined) Chapters 16 and 17 are the complete article.
Schenk, J. L, et al., "Imminent Commercialization of Sexed Bovine Sperm", Proceedings, The Range Beef Cow Symposium XVL, p. 89-96 (1999).
Schenk, J. L., "Cryopreservation of Flow-Sorted Bovine Spermatozoa", Therio. vol. 52, 1375-1391 (1999).
Schiewe, M. C., et al., "Transferable Embryo Recovery Rates Following Different Insemination Schedules in Superovulated Beef Cattle" Therio. 28 (4) Oct. 1997, pp. 395-406.
Schillo, K. K., et al., "Effects of Nutrition and Season on the Onset of Puberty in the Beef Heifer." J. Anim. Sci. 70:3994 (1992).
Schmid, R. L., et al., "Fertilization with Sexed Equine Spermatozoa Using Intracytoplasmic Sperm Injection and Oviductal Insemination", 7th International Symposium On Equine Reproduction, p. 139 (1998) abstr.
Schnell, T. D., et al., "Performance, Carcass, and Palatability Traits for Cull Cows Fed High-Energy Concentrate Diets for 0, 14, 28, 42, or 56 days." J. Anim. Sci. 75:1195. (1997).
Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.
Seidel, G. E. Jr. Sexing mammalian spermatozoa and embryos-state of the art Journal of Reproduction and Fertility Supp 54, 477-487 1999.
Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).
Seidel, G. E. Jr et al., "Current Status of Sexing Mammalian Spermatozoa," Society for Reproduction and fertiity, pp. 733-743, 2002.
Seidel, G. E. Jr., "Commercilizing Reproductive Biotechnology—The Approach used by XY, Inc.," Theriogenology, p. 5, 1999.
Seidel, G. E. Jr. et al., "Insemination of Heifers with Sexed Sperm", Therio, vol. 52, pp. 1407-1421 (1999).
Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.
Seidel, G. E. Jr., "Artificial Insemination With X-and Y-Bearing Bovine Sperm", Animal Reproduction and Biotechnology Laboratory, Colorado State University, (1996).
Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).
Seidel, G. E. Jr., et al., "Insemination of Heifers with Very Low Numbers of Frozen Spermatozoa", CSU, Atlantic Breeders Cooperative, Lancaster, PA, DUO Dairy, Loveland, CO, Jul. 1996.
Seidel, G. E. Jr., et al., "Sexing Mammalian Sperm—Overview", Therio. 52: 1267-1272, (1999).
Seidel, G. E. Jr., et al., "Artificial Insemination of Heifers with Cooled, Unfrozen Sexed Semen", Therio, vol. 49 p. 365 (1998) abstr.
Seidel, G. E. Jr., et al., "Insemination of Heifers with Sexed Frozen or Sexed Liquid Semen." Therio. 51. (in press) (1999) abstr.
Seidel, G. E. Jr., Economics of Selecting for Sex: The Most Important Genetic Trait, Theriogenology 59, (2003), pp. 585-598.
Senger, P. L., et al., "Influence of Cornual Insemination on Conception in Dairy Cattle." J Anim. Sci. 66:3010-3016. (1988).
Shabpareh, V. "Methods for Collecting and Maturing Equine Oocytes in Vitro" Theriogenology 40: 1161-1175, 1993.
Shackelford, S. D., et al., "Effects of Slaughter Age on Meat Tenderness and USDA Carcass Maturity Scores of Beef Females." J. Anim. Sci. 73:3304. (1995).
Shapiro, Howard M. MD., PC. "Practical Flow Cytometry Third Edition," New York 1994.
Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 ABSTRACT.
Shelton, J. N. and Moore, N.W. "The Response of the Ewe to Pregnant Serum Mare Gonadotropin and to Horse Anterior Pituitary Extract." J. Reprod. Fertil. 14:175-177. (1967).
Shilova, A. V., et al., "The Use of Human Chorionic Gonadotropin for Ovulation Date Regulation in Mares." Vlllth Int. Congress On Anim. Repro, and A. I. 204-208. (1976).
Shorthose, W. R. and P. V. Harris. "Effect of Animal Age on the Tenderness of Selected Beef Muscles." J. Food Sci. 55:1-. (1990).
Skogen-Hagenson, M. J. et al.; "A High Efficiency Flow Cytometer," The Journal of Histochemistry and Cytochemistry, vol. 25, No. 7, pp. 784-789, 1977, USA.
Smith, G. C., et al., "USDA Maturity Indexes and Palatability of Beef Rib Steaks." J. of Food Quality 11:1.(1988).
Smith, G. C., et al., "Relationship of USDA Maturity Groups to Palatability of Cooked Beef." J. of FoodSci. 47:1100. (1982).
Solsberry G.U., Van-Denmark N.L., Theory and practice of artificial cow insemination in USA, Moscow, KOLOS Publishing House, 1966, p. 346.
Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

(56) References Cited

OTHER PUBLICATIONS

Spectra-Physics Products, "Fcbar" http://www.splasers.com/products/oem_products/ov_fcbar.html two pages printed Nov. 14, 2002.
Squires, E. L, et al., "Effect of Dose of GnRH Analog on Ovulation in Mares." Therio. 41:757-769. (1994).
Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).
Squires. E. L., "Early Embryonic Loss" *Equine Diagnostic Ultrasonography*, first ed.. Rantanen & McKinnon. Williams and Wilkins, Baltimore, Maryland, p. 157-163 (1998).
Squires, E. L., et al., "Cooled and Frozen Stallion Semen", Bulletin No. 9, Colorado State University, Ft. Collins, CO. (1999).
Staigmiller, R.B. "Superovulation of Cattle with Equine Pituitary Extract and Porcine FSH" Theriogenology 37: 1091-1099 1992.
Stap J. et al. Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.
Steinkamp: "Flow Cytometry" vol. 55, No. 9, Sep. 1984 pp. 1375-1400, New York Review of Scientific Instruments Abstract Only.
Stellflug, J. N., "Plasma Estrogens in Periparturient Cow." Therio 10:269. (1978).
Stevenson, J. S., et al., "Detection of Estrus by Visual Observation and Radiotelemetry in Peripubertal, Estrus-Synchronized Beef Heifers." J. Anim. Sci. 74:729. (1996).
Story, C. E., et al., "Age of Calf at Weaning of Spring-Calving Beef Cows and the Effect on Cow and Calf Performance and Production Economics." J. Anim. Sci. 78:1403. (2000).
Stovel R.T. A Means for Orienting Flat Cells in flow systems Biophysical Journal, 1978,vol. 23,pp. 1-5.
Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).
Sumner, A. T. and Robinson, J. A., "A Difference in Dry Mass Between the Heads of X and Y-Bearing Human Spermatozoa", J Reprod Fertil. 48, p. 9-15 (1976).
Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.
Taljaard, T. L., et al., "The Effect of the Laparoscopic Insemination Technique on the Oestrus Cycle of the Ewe." J. South Afr. Vet. Assoc. 62(2): 60-61. (1991).
Tatum, J. D., et al., "Carcass Characteristics, Time on Feed and Cooked Beef Palatability Attributes." J. Anim. Sci. 50:833. (1980).
Tervit, H.R., et al., "Successful Culture In Vitro of Sheep and Cattle Ova", Agricultural Research Council, Unit of Reprod. Physio, and Biochem., Univ of Cambridge, p. 493-497 (1972).
Thun, Rico, et al., Comparison of Biociphos-Plus® and TRIS-Egg Yolk Extender for Cryopreservation of Bull Semen; Theriogenology Symposium, Dec. 1999, vol. 52, #8.
*Time-Bandwidth Products* "GE-100-XHP", www.tbsp.com. 2 pages. Jan. 2002.
Unruh, J. A. "Effects of Endogenous and Exogenous Growth-Promoting Compounds on Carcass Composition, Meat Quality and Meat Nutritional-Value." J. Anim. Sci. 62:1441. (1986).
USDA "Official United States Standards for Grades of Carcass Beef." Agric, Marketing Serv., USDA, Washington, DC. (1997).
Van Dilla, Martin, "Overview of Flow Cytometry: Instrumentation and Data Analysis", Flow Cytometry: Instrumentation and Data Analysis, Van Dilla et al. (Eds.), 1985, pp. 1-8.
Van Munster, E. B., et al., "Difference in Volume of X- and Y-chromosome Bearing Bovine Sperm Heads Matches Difference in DNA Content" Cytometry vol. 35 p. 125-128 (1999).
Van Munster, E. B., et al., "Measurement-Based Evaluation of Optical Path Length Distributions Reconstructed From Simulated Differential Interference Contrast Images", J of Microscopy 191, Pt. 2, p. 170-176 (1998).
Van Munster, E. B., et al., "Reconstruction of Optical Pathlength Distributions From Images Obtained by a Wide Field Differential Interference Contrast Microscope", J of Microscopy 188, Pt. 2, p. 149-157 (1997).
Vazquez, J. J. et al., "Nonsurgical Uterotubal Insemination in the Mare", Proceedings of the 44th Annual Convention of the American Association of Equine Practitioners, vol. 44, pp. 68-69 (1998).
Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.
Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.
Vidament, M., et al., "Equine Frozen Semen Freezability and Fertility Field Results." Therio. 48:907. (1997).
Vincent, B.C., et al., "Carcass Characteristics and Meat Quality of Once-Calved Heifers." Canadian J. Anim. Sci. 71:311. (1991).
Vogel, T., et al., "Organization and Expression of Bovine TSPY", Mammalian Genome, vol. 8, pp. 491-496 (1997).
Voss, J. L. and Pickett, B. W., "Reproductive Management of the Broodmare." CSU Exp. Sta. Anim. Reprod. Lab. Gen. Series. Bull. 961. (1976).
Voss, J. L., et al., "Effect of Number and Frequency of Inseminations on Fertility in Mares." J. Reprod. Fertil. Suppl. 32:53-57. (1982).
Voss, J. L., et al., Effect of Human Chorionic Gonadotropin on Duration of Estrous Cycle and Fertility of Normally Cycling, Nonlactating Mares. J.A.V.M.A. 165:704-706. (1974).
Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.
Watson, "Recent Developments and Concepts in the Cryopreserwation of Spermatozoa and the Assessment of Their Post-Thawing Function," Reprod. Fertil. Dev. 7:871-891 (1995) ABSTRACT.
Welch G., et al., Fluidic and Optical Modifications to a FACS IV for Flow Sorting of X- and Y-Chromosome Bearing Sperm Based on DNA. Cytometry 17 (Suppl. 7): 74. (1994).
Welch, G., et al., "Flow Cytometric Sperm Sorting and PCR to Confirm Separation of X- and Y-Chromosome Bearing Bovine Sperm", Animal Biotechnology, 6, pp. 131-139 (1995).
Wheeler, T. L., et al., "Effect of Marbling Degree on Beef Palatability in Bos-taurus and Bos-indicus cattle." J. Anim. Sci. 72:3145. (1994).
Wickersham, E. W. and L. H. Schultz. "Influence of Age at First Breeding on Growth, Reproduction, and Production of Well-Fed Holstein Heifers." J. Dairy Sci. 46:544. (1963).
Wilhelm, K.M. et al., "Effects of Phosphatidylserine and Cholesterol Liposomes on the Viability, Motility, and Acrosomal Integrity of Stallion Spermatozoa Prior to and after Cryopreservation", Cryobiology 33:320, 1996.
Wilson, C. G., et al., "Effects of Repeated hCG Injections on Reproductive Efficiency in Mares." Eq. Vet Sci. 4:301-308. (1990).
Wilson, M.S. "Non-surgical Intrauterine Artificial Insemination in Bitches Using Frozen Semen." J. Reprod. Fertil. Suppl. 47:307-311. (1993).
Windsor, D. P., et al., "Sex Predetermination by Separation of X and Y Chromosome-bearing Sperm: A Review", Reproduction of Fertilization and Development 5, pp. 155-171, (1993).
Woods, G. L. and Ginther, O. J. "Recent Studies Related to the Collection of Multiple Embryos in Mares." Therio. 19:101-108. (1983).
Woods, J., et al., "Effects of Time of Insemination Relative to Ovulation on Pregnancy Rate and Embryonic-Loss Rate in Mares." Eq. Vet. J. 22(6): 410-415. (1990).
Zhou, Hongwei, et al. "Research on and Development of Flow Cell Sorting Apparatuses," Gazette of Biophysics, vol. 13, ed. 3, 1997.

(56) References Cited

OTHER PUBLICATIONS

Hamamatsu. "*Photomultiplier Tubes*," web page. http://www.optics.org/hamamatsu/pmt.html Printed on Apr. 15, 2000 4.
Seidel, G. E. Jr., "Fertility of Bulls on the Edge of the Dose—Response Curve for Numbers of Sperm per Inseminate"; Proceedings of the 17th Technical comference on Artificial Insemination & Reproduction, 1998.
Hollinshead, F.K. et al. "In vitro and in vivo assessment of functional capacity of flow cytometrically sorted ram spermatozoa after freezing and thawing." Reprod. Fertil. and Develop. 2003. vol. 15, pp. 351-359.
Hollinshead F. K. et al. "Production of lambs of predetermined sex after the insemination of ewes with low Numbers of frozen-thawed sorted X-or Y-Chromosome-bearing spermatozoa", Reprod. Fertil. and Develop. 2002, vol. 14, pp. 503-508.
Hollinshead F. K. et al. "Sex-Sorting and Re-cryopreservation of Frozen-Thawed Ram Sperm for In Vitro Embryo Production" Theriogenology , vol. 59. (2003) p. 209.
Dhali et al. Vitrification of Buffalo (*Bubalus bubalis*)Oocytes, Embryo Theriogenology vol. 53, pp. 1295-1303 (2000).
Borini et al. Cryopreservation of Mature Oocytes: The use of a trypsin inhibitor enhances fertilization and obtained embryos rates, Fertil. Steril. (1997), vol. 68 (Suppl.).
Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.
Peters D., The LLNL high-speed sorter: Design features,operational characteristics, and bioloical utility, Cyometry, 6:290-301 (1985).
Rens W., et al. Slit-scan flow cytometry for consistent high resdolution DNA analysis of X-and Y-chromosome bearing sperm, Cytometry 25:191-199 (1996).
Van Munster, E. B. Interferometry in flor to sort unstained X- and Y-Chromosome-Bearing Bull Spermatozoa, Cytometry 47:192-199 (2002).
Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.
Brink, Z et al. A reliable procedure for superovulating cattle to obtain zygotes and early emryos for microinjection, Theriogenology vol. 41, p. 168, (1994).
Fluorescense Lifetime Systems, www.picoquant.com, Jan. 28, 2005 pp. 2.
NCI ETI Branch, Flow CytometryCore Laboratory, http://home.ncifcrf.gov/ccr/flowcore/ndyag.htm, pp. 5, May 11, 2004.
NCI ETI Branch, Flow CytometryCore Laboratory, http://home.ncifcrf.gov/ccr/flowcore/lsrll.htm, pp. 14, May 11, 2004.
Saacke.R.G., Can Spermatozoa with abnormal heads gain access to the ovum in artificially inseminated super-and single-ovulating cattle?, Theriogenology 50:117-128. 1998.
Hawk, H.W., Gamete Transport in the Superovulated Cow. Theriogenology: Jan. 1998 vol. 29 No. 1 pp. 125-142.
Blecher, S.R. , et al. A new approach to immunological sexing of sperm, Theriogenology, 59, pp. 1309-1321, 1999 vol.
Wheeler, M. B., et al. Application of sexed semen technology to in vitro embryo production in cattle, Theriogenology, vol. 65 (2006) 219-227.
Bodmer, M., et al., Fertility in heifers and cows after low does insemination with sex-sorted and non-sorted sperm under field conditions; Theriogenology, vol. 64, (2005) 1647-1655.
Schenk J. L., et al. Embryo production from superovulated cattle following insemination of sexed sperm, Theriogenology, 65 (2006) 299-307.
Gamer, D. L., Flow cytometric sexing of mammalian sperm, Theriogenology, 65 (2006) 943-957.
Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).
Johnson, L. A., Sexing mammalian sperm for production of offspring: the state-of-the-art; Animal Reproduction Science; 60-61 (2000) pp. 93-107.
Seidel, G.E. Jr., et al., Methods of Ovum Recovery and Factors Affecting Fertilization of Superovulated Bovine Ova, Control of Reproduction in the Cow, Sneenan ed., 1978, pp. 268-280.
Hawk, H. W. et al., Effect of Unilateral Cornual Insemination upon Fertilization Rate in Superovulating and Single-Ovulating Cattle, Journal of Animal Sciences, 1986 vol. 63, pp. 551-560.
Andersson, M. et al., Pregnancy Rates in Lactating Holstein-Greisian Cows after Artificial Insemination with Sexed Sperm. Reprod. Dom. Anim 41, 95-97, 2006.
Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.
Wilson, R. D., et al., In vitro production of bovine embryos using sex-sorted sperm, Theriogenology, 65 (2006) 1007-1015.
Bracher, V. and Allen, W.R., "Videoendoscopic Examination of the Mare's Uterus: I. Findings in Normal Fertile Mares", Equine Veterinary Journal, vol. 24, p. 274-278. 1992.
Johnson, L.A., "Flow Cytometric Determination of Spermatozoa Sex Ratio In Semen Purportedly Enriched for X or Y Bearing Spermatozoa", Therio. 1988 29:265 abstr.
Lindsey, A., et al., "Hysteroscopic Insemination of Mares with Nonfrozen Low-dose Unsexed or Sex-sorted Spermatozoa", pp. 1-15, 2000.
Lu, K. H. et al., "In Vitro Fertilization of Bovine Oocytes with Flow-Cytometrically Sorted and Unsorted Sperm from Different Bulls" Therio. 2001 abstr.
Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.
Sell, R. S., et al., "Single-calf Heifer Profitability Compared to Other North Dakota Beef Production Systems." Department of Ag. Eco., North Dakota State University, Ag. Econ. Rpt 20.; Oct. 1988.
Smith, R. L., et al., Influence of Percent Egg Yolk during Cooling and Freezing on Survival of Bovine Spermatozoa, Dairy Science 1979 J 62:1297-1303.
Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.
Van Munster, E. B., et al., "Difference in Sperm Head Volume as a Theoretical Basis for Sorting X & Y-Bearing Spermatozoa: Potentials and Limitations", Therlo 52, pp. 1281-1293 (1999).
Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.
Vazquez, J., et al., "Hyposmotic Swelling Test as Predictor of the Membrane Integrity in Boar Spermatozoa", Boar Semen Preservation IV, IVth International Conference on Boar Semen Preservation, Maryland, p. 263., Jun. 2004.
Hermesmeyer, G.N. , et al. Effects of Lactation and Prenatal Androgenization on the Performance, Carcass Composition, and Longissimus muscle sensory characteristics of heifers in the single-calf heifer system. The Professional Animal Scientist 15:14-23, (1995).
Johnson, L.A, et al., 1996 Gender preselection in mammals. XX Beltsville Symposium in Agricultural Research Technolgy's Role in the Genetic Improvement of Farm Animals, pp. 151-164, Amer. Soc. Anim. Sci. IL. USA.
Smorag, Z., et al.. Cattle Sex Regulation by Separation of X and Y Spermatozoa—Preliminary Results of Field Experiment In Poland, Reproduction, Fertility and Development 17(2) 306-306; Jan. 1, 2005.
Crichton, E., et al. (Abstract) Artificial Insemination of Lactating Holstein Cows with Sexed Sperm, Reproduction, Fertility and Development 18(2) 281-281, Dec. 14, 2005.

(56) References Cited

OTHER PUBLICATIONS

Lindsey, A.C., et al. Hysteroscopic insemination of low numbers of flow sorted fresh and frozen/thawed stallion spermatozoa, Equine Vet J. Mar. 2002;34(2):106-7.
Drobnis, E. Z, Cold shock damage is due to lipid phase transitions In cell membranes ; a demonstration using sperm as a model, Journal of experimental zoology (J. exp. zool.) 1993, vol. 265, No. 4, pp. 432-437 (22 ref.).
Hagele, W.C., et al., Effect of Separating Bull Semen into X and Y Chromosome-bearing Fractions on the Sex Ratio of Resulting Embryos; Cran J. Comp. Med, 1984: 48:294-298.
Suh, T.K, et al., Pressure during flow sorting of bull sperm affects post-thaw motility characteristics; Theriogenology vol. 59, No. 1, Jan. 2003 p. 516.
Rath, D, et al., In Vitro Production of Sexed Embryos for Gender Preselection: High-speed sorting of X-Chromosome-Bearing Sperm to Produce Pigs After Embryo Transfer. J. Anim. Sci. 1999. 77:3346-3352.
Auchtung, T.L., et al., Effects of Photoperiod During the Dry Period on Prolactin, Prolactin Receptor, and Milk Production of Dairy Cows; Journal of Dairy Sci. 88: 121-127: American Dairy Sci. Assoc., 2005.
Bailey, T. et al., Milk Production Evaluation In First Lactation Heifers; 1999 Virginia Cooperation Extension/Dairy Science Publication 404-285.
Belloin, J.C., Milk and Dairy products: prductlon and processing costs Food and Agriculture Organization of United Nations Rome 1988 FAO; web page where found: www.fao.org/docrep/003/x6931e/X6931E00.htm.
Lopez, H. et al., Relationship Between Level of Milk Production and Multiple Ovulation in Lactating Dairy Cows Journal of Dairy Sci. 88:2783-2793; American Dairy Science Association, 2005.
Milk Production and Biosynthesis University of Guelph/Dairy Science and Technology (1998) www.foodsci.uoguelph.ca/dairyedu/biosyntheses.html.
Milk Production, Released Jul. 18, 2006, by the National Agricultural Statistics Service (NASS), Agri. Stats. Board, US Dept of Agri.
De Vries, A. Economic Value of Pregnancy In Dairy Cattle Journal of Dairy Sci. 89:3876-3885/Amerlcan Dairy Sci. Assoc. 2006.
Gamer, D.L. et al., Viability Assessment of Mammalian Sperm Using SYBR-14 and Propidium Lodide, 1996, Biology of Reporduction, vol. 53, pp. 276-284.
Salisbury, G.W. et al., Substrate-Free Epididymal-Like Bovine Spermatozoa, J Repord Fertil, 1963, vol. 6. pp. 351-359.
Wong, P.Y.D., et al. Potassium Movement During sodium-induced Motility Initiation in the Rat Caudal Epididymai Spermatozoa; Biology of Reproduction 28, 206-212 (1983).
Shirai, H., et al. Regulation of Sperm Motility in Starfish; Development, Growth, and Differentiation; 24, (5), 419-428 (1982).
Padilla, A.W. et al. Extender and Centrifugation Effects on the Motility Patterns of Slow-Cooled Stallion Spermatozoa; J. Anim. Sci 1991, 69:3308-3313.
McGrady, A.V., et al. Cholinergic Effects on Bull and Chimpanzee Sperm Motility; Biology of Reproduction 15, 248-253 (1976).
Jones, J.M. et al. Acidification of Intracellular pH in Bovine Spermatozoa Suppresses Motility and Extends Viable Life, Journal of Andrology, vol. 21, No. 5, September/October 616-624.
Jenkins, A. D., et al. Concentrations of Seven Elements in the Intraluminal Fluids of the Rat Seminiferous Tubules, ReteTestis, and Epididymis; Biology of Reproduction 23, 981-987 (1980).
Darszon, A., et al. Ion Channels in Sperm Physiology, Physiological Reviews, vol. 27, No. 2, Apr. 1999.
Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.
Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Purdy, P. H. et al., Effect of Adding Cholesterol to Bull Sperm Membranes on Sperm Capacitation, the Acrosome Reaction, and Fertility, Biology of Reproduction 71, 522-527 (2004).
Purdy, P. H. et al., Effect of cholesterol-loaded cyclodextrin on the cryosurvival of bull sperm, Cryobiology 48 (2004) 36-45.
Moce E., et al., Cholesterol-loaded cyclodextrins added to fresh bull ejaculates improve sperm cryosurvival, J. Anim. Sci, 2006, 84:826-833.
Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.
United States Office Action dated Aug. 20, 2014, issued in related U.S. Appl. No. 11/668,148 (17 pp).
U.S. Petition for Inter Partes Review No. 2014-01550 filed Sep. 29, 2014, (73 pp).
Declaration and Curriculum Vitae of Marvin M. Pace as filed in inter Partes Review No. 2014-01550 dated Sep. 26, 2014 (139 pp).
Polge, C. and Rowson, L.E.A., "Long-term Storage of Bull Semen Frozen at Very Low Temperatures (-79° C.)" in "Report of The II. International Congress of Physiology and Pathology of Animal Reproduction and of Artificial Insemination," vol. 111 (1952).
LaSalle, B., "Introduction" in "The Integrity of Frozen Spermatozoa, Proceedings of a Round-Table Conference held on Apr. 6-7, 1976," National Academy of Sciences (1978).
Herman, H.A. and Madden, F.W., "The Artificial Insemination of Dairy and Beef Cattie: A Handbook and Laboratory Manual" 6th Ed. (1980).
Graham, E.F., "Fundamentals of the Preservation of Spermatozoa," in "The Integrity of Frozen Spermatozoa, Proceedings of a Round-Table Conference held on Apr. 6-7, 1976," National Academy of Sciences (1978).
Berndtson, W.E. and Pickett, B.W, "Techniques for The Cryopreservation and Field Handling of Bovine Spermatozoa," in "The Integrity of Frozen Spermatozoa, Proceedings of a Round-Table Conference held on Apr. 6-7, 1976," National Academy of Sciences (1978).
Bulletin 621, "Preservation of Bull Semen at Sub-Zero Temperatures," University of IL Ag. Exp. Station (1957).
Doak, "CSS Implementation of New Antibiotic Combination," Proceedings of the 11th Tech. Conf. on Art. Insemination and Reproduction (1986).
A. A. Luderer, "Separation of Bovine Spematozoa by Density on Water insoluble Newtonian Gels and Their Use for insemination," Bio. of Repro., vol. 26, pp. 813-824 (1982).
Beal. W.E., et al. "Sex Ratio after Insemination of Bovine Spermatozoa Isolated using a Bovine Serum Albumin Gradient," 58 J. Anim. Sci. 1432-36 (1984).
Foote. "Normal Dev. of Fetuses Resuiting from Holstein Semen Processed for Sex Sevaration," Theriogenoloqy, vol. 24, No. 1, pp. 197-2002 (1985).
The American Heritage College Dictionary, 3rd Ed. (1997) Houghton Mifflin Company, Boston-New York, pp. 387. 543-544, 1242-1243.
Bakst, M.R., "Fate of fluorescent stained sperm following insemination: New light on Oviducal Sperm Transport and Storage in the Turkey", Biology of Reproduction, 1994, vol. 50, No. 5, pp. 987-992.
Cho, B., et al., "A microfluidic device for separating motile sperm from nonmotile sperm via inter-streamline crossings", Microtechnologies in Medicine & Biology 2nd Annual International IEEE-EMB Special Topic Conference on, pp. 156-159. IEEE, 2002.
Centola, G. M., et al., "Cryopreservation of Human Semen. Comparison of Cryopreservatives, Sources of Variability, and Prediction of Post-thaw Survival." Journal of Andrology 13.3 (1992): 283-288, Abstract 1 pp.
Courtens, J., et al., "Numerical simulation for freezing and thawing mammalian spermatozoa. Evaluation of cell injuries at different depths in bags or straws during all steps of the technique", Genetics Selection evolution, vol. 33 (2001): S85-S104, 11 pp.
Durack, G., et al., "Cell-Sorting Technology", Emerging Tools for Single-Cell Analysis: Advances in Optical Measurement Technologies, 2000 Wiley-Liss, Inc., New York, Chapter 1, pp. 1-19.

(56) References Cited

OTHER PUBLICATIONS

Ericsson, R., et al., "Functional differences between sperm bearing the X-or Y-chromosome", Prospects for Sexing Mammalian Sperm, RP Amann and GE Seidel, Jr., eds. (1982): 6 pp.

Fitzgerald, D.A., "Cell sorting: An enriching Experience", Scientist Magazine-Philadelphia—15.15 (2001): 28-29 (4 pp printed Jul. 29, 2014).

Foote, R. H. "Functional differences between sperm bearing the X-or Y-chromosome." Prospects for Sexing Mammalian Sperm, RP Amann and GE Seidel, Jr., eds. (1982): 3 pp.

Garner, D. L., et al., "Past, present and future perspectives on sexing sperm." Canadian Journal of Animal Science CSCS Symposium 83.3 (2003): pp. 67-78.

Johnson, L. A., et al., "Sex preselection in mammals by DNA: A method for flow separation of X and Y Spermatozoa in humans." Manual on Assisted Reproduction. Springer Berlin Heidelberg, 1997. 337-349.

Garner, D. L., et al., "Chromatin stability in sex-sorted sperm." VII International Congress of Andrology, 2001, p. 162 (Abstract).

Garner, D. L., et al., "Spermatozoa and Seminal Plasma." Reproduction in Farm Animals 7th Ed. (2000) Lippincott, Williams & Wilkins, Philadelphia, PA: pp. 96-99.

IMV Technologies,"Protocol of Bioxcell with Frozen Semen", 2 pp.

Givan, Alice Longobardi, "Flow Cytometry: First Principles," 1992, WileyLiss Inc., New York, 120 pp.

Gledhill, et al., "Identifying X-and Y-chromosome-bearing sperm by DNA content: retrospective perspectives and prospective opinions", No. UCRL-87315; CONF-820349-1. Lawrence Livermore National Lab., Dept. of Physiological Sciences, Conference on prospects of sexing mammalian sperm, Mar. 18, 1982, 8 pp.

Gerrits, Roger J. "Application of Biotechnology to Animal Production", Proc. of 2nd Int'l Conference on Boar Semen Preservation, Supplement to Reprod. in Dom. Animals (1991) pp. 221-228.

Hargrove, T. et al., "Special Techniques." Part B Cryopreservation, Chapter 11B (1996) pp. 219-222.

Harte, F. J., "System of Production of Beef from once calved Heifers", Early Calving of Heifers & Its Impact On Beef Production; Proceedings of A Seminar On Nutrition & Management, 1975, pp. 123-127.

Gurnsey, M.P., et al., "Recent improvements in efficiency of flow cytometric sorting of X and Y-chromosome bearing sperm of domestic animals: A review," Proceedings—New Zealand Society of Animal Production, New Zealand Society of Animal Production Publ., vol. 58. 1998, (Abstract) 3 pp.

Göttlinger, C., et al., "Operation of a Flow Cytometer" Flow Cytometry and Cell Sorting, Springer Laboratory1992, pp. 7-23.

Graham, J., "Analysis of stallion semen and its relation to fertility", The Veterinary Clinics of North America. Equine Practice,1996, 12(1):119-130.

Jeyendran, R. S., et al., "Effect of Glycerol and Cryopreservation on Oocyte Penetration by Human Spermatozoa," Andrologia vol. 17.3 (1985): 241-248 (Abstract).

Johnson, L. A. "Verified sex pre-selection in farm animals", Proceedings of the 2nd Int. Conf. on Boar Semen Pres. Belrin and Hamburg: Paul Parey Sci. Publishers, (1990) pp. 213-219.

Johnson, M. H. "The macromolecular organization of membranes and its bearing on events leading up to fertilization." Journal of reproduction and fertility 44.1 (1975): 167-184.

Johnson, L.A., et al., "Sex preselection in swine: flow cytometric sorting of X-and Y-chromosome bearing sperm to produce offspring", Boar Semen Preservation IV, 107-114 (2000).

Johnson, L.A., "Successful gender preselection in farm animals", Agricultural Biotechnology (1998) Marcel Dekker, Inc., New York, pp. 439-452.

Lindsey, A.C., et al., "Hysteroscopic Insemination of Mares using non-sorted and sex-sorted sperm", Animal Reprod. Science, vol. 68 (2001) 279-289.

Masaki, J. et al., "Effect of bull seminal plasma on the membrane characteristics of boar epididymal spermatozoa", AGRIS, National Agriculture Library (1984) 3 pp.

Meistrich, M.L., "Potential and limitations of physical methods for separation of sperm bearing an X-or Y-chromosome", Prospects for sexing mammalian sperm (RP Amann and GE Seidel eds.), Colorado Associated University Press, Boulder, Colorado (1982): 157-168.

Murthi, S., et al., "Improved data acquisition system for digital flow cytometry ", Circuits and Systems, ISCAS, 2002 IEEE International Symposium on (vol. 1 ) pp. I-669-I-672.

Parks, J., "Processing and handling bull semen for artificial insemination—Don't add insult to injury", Department of Animal Science Cornell University , 6 pp.

Polge, C., "Low-temperature storage of mammalian spermatozoa", Proceedings of the Royal Society of London. Series B-Biological Sciences 147 No. 929 (1957): 498-508.

Saacke, R.G. et al., "Semen quality tests and their relationship to fertility." Proc. of the Fourth Tech. Conf. on Artificial Insemination and Reproduction, National Association of Animal Breeders, Columbia, MO, USA. 1972, pp. 22-27.

Tone, S., et al., "A method of vital staining of mouse eggs using Hoechst dye", Japanese Journal of Animal Reproduction, 32 (1986) pp. 101-105.

Amann, R.P., "Prospects for sexing mammalian sperm", Colorado University Press Conference Proc., Mar. 19-20, 1982, pp. 253-282.

Asbury, C.L., "Fluorescence spectra of DNA dyes measured in a flow cytometer", Cytometry, vol. 24, Issue 3, pp. 234 242, 1996.

Bigos, M., et al., "Nine color eleven parameter immunophenotyping using three laser flow cytometry", Cytometry 36.1 (1999): 36-45.

Bioxcell, Bovine Sperm Preservation, Advertisement Jun. 28, 2005, 1p.

Cran, D.G., et al., "Production of lambs by low dose intrauterine insemination with flow cytometrically sorted and unsorted semen", Theriogenology vol. 47 No. 1 (1997): pp. 267.

Crowley, J. P. "The facts of once-bred heifer production." School of Agric., Univ. of Aberdeen, Scotland (1973) pp. 8-17.

DakoCytomation.us, MoFlo Sorters http://ww1.dakocytomation.us/prod_productrelatedinformation?url=gprod_moflo_index.htm, printed Jun. 26, 2003, 1 p.

Denham, A., "In-vitro studies on Sandhill Range Forage as Related to Cattle Preference", Diss. MS Thesis. Colorado State University, 1965, 6 pp.

Ereth, B.A., et al., Integration of Early Weaning and Sexed Semen into a Single-Calf Heifer System to Increase Value of Non-Replacement Heifers; In Proceedings-American Society of Animal Science Western Section, vol. 51, pp. 441-443. 2000, Abstract Only, Journal of Animal Science, 2000.

Fuller, R. R., et al., "Characterizing Submicron Vesicles With Wavelength-Resolved Fluorescence in Flow Cytometry", Cytometry 25 (1996): 144-155.

Hamamatsu, "Photomultiplier Tubes," web page, http://www.optics.org/hamamatsu/pmt.html. Printed on Apr. 15, 2000, 4 pp.

Hanania, E. G, et al. "A Novel Automated Method of Scanning Cytometry and Laser-Induced Necrosis Applied to Tumor Cell Purging" Abstract#2836, In Blood (vol. 94, No. 10, p. 638A-639A) 1999.

Pickett, B.W., et al., "Recent developments in artificial insemination in horses", Livestock Production Science, 40 (1994) 31-36.

Pinkel, D. et al., "Flow chambers and sample handling", Flow Cytometry: Instrumentation and Data Analysis (1985): 77-128.

Piston, D.W., et al., "Three-dimensionally resolved NAD (P) H cellular metabolic redox imaging of the in situ cornea with two-photon excitation laser scanning microscopy", Journal of Microscopy, vol. 178, Issue 1, (1995) pp. 20-27.

Rieger, D., et al., "The relationship between the time of first cleavage of fertilized cattle oocytes and their development to the blastocyst stage", Theriogenology 51.1 (1999): 190.

Schenk, J.L., "Applying Semen Sexing Technology to the AI Industry", Proceedings of the 18th Technical Conference on Artificial Insemination & Reproduction, 2000, pp. 73-78.

Seidel, G.E. Jr., et al., "Insemination of Holstein heifers with very low numbers of unfrozen spermatozoa"' Csu, Atlantic Breeders Cooperative (1995) 1 pp.

Seidel, G. E. Jr. " Sexing Bovine Sperm" The AABP Proceedings— (2001) vol. 34, pp. 106-108.

(56) References Cited

OTHER PUBLICATIONS

Spectra-Physics, The Solid State Laser Company, Vanguard 350-HMD 355 Specifications, 2002, 3 pp.
Spectra Physics, The Solid State Laser Company, "Vangaurd 4 Watts of Uv from a Quasi-CW, All Solid State Laser," http://www.splasers.com/products/isl_products/vangaurd.html, 3 pp, printed Nov. 14, 2002
Brazilian Office Action dated Apr. 10, 2015 in related BR Patent Application No. PI 0314218.3.
U.S. Office Action dated Jun. 29, 2015 in related U.S. Appl. No. 11/668,148.
Medvedev. S, et al. Intracytoplasmic Sperm Injection (ICSI) With Flow Cytometrically Sorted Y-Chromosome Bearing Sperm. Theriogenology 47:270 (1997).
EP Examination Report dated Sep. 3, 2015 issued in Related EP Application No. 10186250.6.
Office Action dated May 31, 2016 issued in related U.S. Appl. No. 11/668,148.
Wheeler, D. J. et al. "Microfluidic Technology for In Vitro Embryo Production." IEEE Xplore Document—Microfluidic technology for in vitro embryo production. 2002. http://ieeexplore.ieee.org/document/1002274/?reload=true&arnumber=100227.
Ince, D. et al. "Effects of Oestrus Synchronization and Various Doses of PMSG Administrations in Chios x Kivircik (F1) Sheep on Reproductive Performances." Journal of Animal and Veterinary Advances 8 (10): 1948-1952, 2009.
Dinnye's, A et al. "High Developmental Rates of Vitrified Bovine Oocytes Following Parthenogenetic Activation, In Vitro Fertilization, and Somatic Cell Nuclear Transfer." Biology of Reproduction 63, 513-518 (2000).
Donnelly, E. et al. "Cryopreservation of Human Semen and Prepared Sperm: Effects On Motility Parameters and DNA Integrity." Fertility and Sterility, vol. 76, No. 5, Nov. 2001.
EP Examination Report dated Dec. 19, 2016 in related EP Appl. No. 10186250.6.
Dalimata et al. "Cryopreservation of Rabbit Spermatozoa Using Acetamide in Combination with Trehalose and Methyl Cellulose." Theriogenology 48: p. 831-841. 1997.
U.S. Office Action dated Sep. 5, 2017 in related U.S. Appl. No. 11/668,148.
EP Examination Report dated Feb. 13, 2018 in related EP Appl. No. 10186250.6.
EP Examination Report dated Jan. 7, 2019 in related EP Appl. No. 10186250.6.
US Office Action dated Jun. 26, 2019 in related U.S. Appl. No. 11/668,148.
EP Examination Report dated Aug. 12, 2019 in related EP Appl. No. 10186250.6.
Valcarcel et al., Comparison between Sephadex G-10 and Percoll for preparation of normospermic, asthenospermic and frozen/thawed ram semen, 1996, Animal Reproduction Science, 41 (3-4): 215-224, abstract (Year: 1996).
Hollinshead et al., Assessment of in vitro sperm characteristics after flow cytometric sorting of frozen-thawed bull spermatozoa, Theriogenology 62 (2004) 958-968 (Year: 2004).
United States Office Action dated Feb. 14, 2014, issued in related U.S. Appl. No. 11/668,148 (20 pp).
Gilbert, Bruce, et al. Effects of serial thaw-refreeze cycles on human sperm motility and viability. Fertility and Sterility, Jun. 2001, vol. 75, No. 6, pp. 1242-1243.
Foote, Robert H., Letter to the Editor. Journal of Andrology, May/Jun. 2000, vol. 21 No. 3, pp. 355.
Polcz, Tibor, et al. Optimal Utilization of Cryopreserved Human Semen for Assisted Reproduction: Recovery and Maintenance of Sperm Motility and Viability. Journal of Assisted Reproduction and Genetics, Sep. 1998, vol. 15, No. 8, pp. 504-512.

\* cited by examiner

SPERM CELL PROCESSING SYSTEMS

CROSS-REFERENCE TO RELATED APPLICATIONS

This application is a continuation application of prior U.S. patent application Ser. No. 11/668,148, filed on Jan. 29, 2007, which is a continuation application of U.S. patent application Ser. No. 10/340,881, filed Jan. 9, 2003, now U.S. Pat. No. 7,169,548, which claims the benefit of prior U.S. Provisional Application No. 60/410,884, filed Sep. 13, 2002, each said foregoing application and any priority case hereby incorporated herein by reference.

BACKGROUND OF THE INVENTION

Fertilization techniques such as artificial insemination and in vitro fertilization techniques have been conducted in attempt to increase the fertility rates of livestock. Furthermore, effective pre-selection of sex has been accomplished in many species of livestock following the development of safe and reliable methods of sorting, generally, or specifically separating sperm cells into enriched X chromosome bearing and Y chromosome bearing populations. Separation of X chromosome bearing sperm cells from Y chromosome bearing sperm cells, as well as collection, handling, sorting, separation, storage, transportation, use, fertilization, or insemination techniques, or sperm cell and semen processing generally, can be accomplished as disclosed herein and as disclosed by various patent applications, for example: PCT/US99/17165; PCT/US01/45023; PCT/US01/15150; PCT/US98/27909; PCT/US01/45237; PCT/US01/18879, PCT/US00/30155, PCT/US01/02304, U.S. Pat. Nos. 6,071, 689, 6,372,422, U.S. divisional application Ser. No. 10/081, 955, U.S. provisional application No. 60/400,486, and U.S. provisional application No. 60/400,971, each included in Exhibit A attached, and each hereby incorporated by reference herein.

Although the various devices and methods of sperm cell processing, generally, and the collection, handling, separation, storage, transportation, usage, fertilization, and insemination of sperm cells have been improved over the past several years, significant problems remain with respect to maintaining sperm quality, such as viability, motility, functionality, and preservation and stimulation relative to such techniques, especially with regard to artificial insemination (in vivo) and in vitro fertilization (IVF) procedures. One potential consequence is the reduction in fertility rates. Sperm quality, such as the viability of sperm separated into enriched X-chromosome bearing and Y-chromosome bearing populations could be compared directly in-vitro (for example, in conjunction with IVF procedures) and in-vivo (for example, in conjunction with artificial insemination procedures), is generally reduced during traditional sperm cell processing. More generally, traditional processing techniques addressing sperm viability, motility, functionality, preservation, stimulation, fertilization, and insemination may have not yielded preferred fertility rates, insemination rates, fertilization rates, or sperm quality, generally.

As one example of traditional sperm processing, techniques of sperm sorting for the breeding of mammals may be limited, for example, with regard to sperm cell quality, such as sperm cell viability, and fertility rates, in circumstances wherein the sorter apparatus is a relatively long distance from the males or when the sorter apparatus is a relatively long distance from the receiving females to be inseminated or otherwise fertilized with processed sperm. Some of the techniques incorporated by reference may achieve to some degree sperm cell viability, motility, or functionality, and desirable fertility rates, while addressing, for example, sperm preservation during transportation to the sorter apparatus. However, further techniques achieving sufficient sperm cell quality, such as viability, motility, functionality, stimulation, and preservation, and maintained or enhanced fertility rates, insemination rates, fertilization rates, may be desirable, especially for any one or a combination of various sperm processing steps, such as, for example, collection, handling, separation, storage, transportation, usage, fertilization, or insemination of semen or sperm cells, especially the preservation of the sorted sperm cells from the sorter apparatus to the site of fertilization (potentially via collected individual samples or "straws"), or at any other stage of sperm processing.

As another example of the limitations of traditional sperm processing, traditional processing techniques may be limited with regard to sperm cell quality, generally, such as sperm cell viability, motility, functionality, stimulation, and preservation, as well as fertility rates, insemination rates, fertilization rates, due to the type and the extent processing involved. Known processing techniques such as preservation or sorting, for example, may degrade sperm quality, and further reduce fertility rates, insemination rates, and fertilization rates. The degradation of sperm quality and/or the reduction of fertility rates, insemination rates, and fertilization rates may have previously proven problematic in circumstances that may have required further steps of sperm cell preservation, such as in circumstances wherein the sorter apparatus is a relatively long distance from the males or when the sorter apparatus is a relatively long distance from the receiving females to be inseminated or otherwise fertilized with processed sperm.

It may have been traditionally understood that additional processing steps in the processing of sperm cells or semen having a concentration of sperm cells would degrade sperm quality and reduce fertility rates, insemination rates, and fertilization rates to such an extent that additional processing steps, generally, would be avoided. Specifically, it may also have been traditionally understood that processing steps such as preservation, specifically cryopreservation, and sorting might be too damaging to the sperm cells, especially in processing sequences incorporating both cryopreservation and sorting. Furthermore, it may have even been suggested and taught in traditional methods that preservation of sperm, such as cryopreservation, provided after previous processing steps so as to preserve the sperm for later procedures, such as for in vivo or in vitro techniques, could not be accomplished without compromising the sperm cells and the technique itself to such a degree that the results of the later procedures would be detrimentally affected. Accordingly, such concerns may have even been demonstrated in traditional sperm cell processing procedures, teaching away from subsequent processing steps such as sorting and cryopreservation, or processing steps incorporating multiple cryopreservation steps.

SUMMARY OF THE INVENTION

The present invention addresses the variety of previously identified and potentially unaddressed problems associated with reduced sperm cell quality, such as viability, motility, functionality, stimulation, and of preservation. Sperm cells that may have been or will be processed by one or more steps of collection, handling, separation, storage, transportation, usage, fertilization, or insemination and potential reductions in fertility rates, insemination rates, or fertilization rates are further addressed. The instant invention also addresses the variety of problems associated with sperm cell quality of sperm cells that have been separated into enriched X-chromosome bearing and Y-chromosome bearing populations, potentially sperm cells separated or sorted through techniques such as flow sorting, and the potential reduction in fertility rates. More generally, the present invention addresses traditionally low fertility rates of in vivo artificial insemination and in vitro fertilization, and sperm cell quality issues such as sperm cell viability, motility, functionality, stimulation, and preservation, as well as fertility rates, insemination rates, fertilization rates, achieving results that may have been unexpected to those skilled in the art. Additionally, the present invention addresses numbers of processed sperm potentially needed to obtain desired pregnancy rates, and further in consideration of pregnancy rates obtained respective of sorted and unsorted preserved sperm.

Accordingly, broad objects of the present invention are to provide systems to address sperm cell quality, such as viability, motility, functionality, and preservation, and to address fertilization rates, insemination rates, and fertilization rates. Each of the broad objects of the present invention may be directed to one or more of the various and previously described concerns.

One object of the present invention is to provide methods and systems of semen and sperm cell processing and preservation, and methods and systems of producing a mammal and methods of producing mammalian embryos. A further object of the present invention is to provide preservation, stimulation, fertilization, and insemination, potentially provided alone or in combination with any one or a combination of various sperm processing steps, such as, for example, collection, handling, separation, storage, transportation, usage, fertilization, or insemination of semen or sperm cells. One related object is to provide such systems in relation to the preservation of sperm cells and one or more sequences of sperm cell processing, such as the preservation of sorted sperm cells, and further in some instances, for example, preservation to a sorter apparatus, preservation from a sorter apparatus, preservation to the site of fertilization (potentially via individual sperm samples or "straws"), or at any other stage of sperm processing.

A related object of the invention is to provide systems of collection, handling, separation, storage, transportation, usage, fertilization, or insemination for semen or sperm cells to achieve desirable levels of fertility rates. One related goal is to provide systems of collection, handling, separation, storage, transportation, usage, fertilization, or insemination to maintain and enhance sperm viability, motility, functionality, preservation, stimulation, and levels of fertility rates.

A third object is to address sperm cell quality, such as sperm cell viability, motility, functionality, stimulation, and preservation, as well as fertility rates, in the context of fertilization and insemination, and in some embodiments, in the context of in vivo or in vitro techniques. A related goal of the present invention is to provide systems that achieve desirable levels of fertility rates. A second goal of the present invention is to provide systems that achieve desirable levels of fertility rates in combination with collection, handling, separation, storage, transportation, fertilization, or insemination techniques, and combinations of such techniques. A third goal of the present invention is to provide systems that achieve individual sperm samples of processed sperm cells, such as straws, of desired viability, motility, functionality, preservation, stimulation, or other characteristics, or combinations of characteristics, potentially resulting in desirable levels of fertility rates. Another related goal is to provide systems that achieve sufficient numbers of processed sperm potentially needed to obtain desired pregnancy rates, and further in consideration of pregnancy rates obtained respective of processing techniques, such as the sorting of sperm cells, and in some cases, sperm or sperm cells previously preserved.

A further object is to address sperm cell quality, such as sperm cell viability, motility, functionality, stimulation, and preservation, as well as fertility rates, insemination rates, fertilization rates, for semen or sperm cells obtained from various species of mammals, including, but not limited to equids, bovids, felids, ovids, canids, buffalo, oxen, elk, or porcine; or obtained from prize, endangered, or rare individuals of a mammal species; or obtained from zoological specimens. A related goal of the present invention, therefore, is to address sperm cell quality, generally, such as sperm cell viability, motility, functionality, stimulation, and preservation, as well as fertility rates, insemination rates, fertilization rates, for semen or sperm cells obtained from various species, individuals, and specimens so as to maintain or enhance sperm viability, motility, functionality, preservation, stimulation, fertility rates, or other characteristics, or combinations of characteristics.

Another object of the invention is to provide systems of collection, handling, separation, storage, transportation, usage, fertilization, or insemination for semen or sperm cells obtained from various species of mammals, including, but not limited to equids, bovids, felids, ovids, canids, buffalo, oxen, elk, or porcine; or obtained from prize, endangered, or rare individuals of a mammal species; or obtained from zoological specimens. A related goal of the present invention, therefore, is to provide systems of collection, handling, separation, storage, transportation, usage, fertilization, or insemination for semen or sperm cells obtained from various species, individuals, and specimens so as to maintain or enhance sperm viability, motility, functionality, preservation, stimulation, fertility rates, or other characteristics, or combinations of characteristics.

An object of the present invention is to provide systems that achieve individual samples of processed sperm, such as straws, of desired sperm cell quality, such as sperm cell viability, motility, functionality, stimulation, and preservation, or other characteristics, or combinations of characteristics, as well as providing desirable levels of fertility rates, insemination rates, or fertilization rates.

Another significant object of the invention is to provide systems of sperm cell separation that can maintain or enhance a greater sperm cell quality, such as sperm cell viability, motility, functionality, stimulation, and preservation, or other characteristics, or combination of characteristics, as well as fertility rates, insemination rates, fertilization rates, for sperm cells throughout a flow sorting process such as a process incorporating a flow cytometer.

Another significant object of the invention can be to provide systems of maintaining or enhancing sperm cells at greater sperm cell quality, such as sperm cell viability, motility, functionality, stimulation, and preservation, or other characteristics, or combination of characteristics, as well as fertility rates, insemination rates, or fertilization rates, for purposes of in vivo insemination or in vitro fertilization of various species, such as those described above, or even insemination with a low or reduced number of sperm cells compared to the usual number or typical number of sperm cells used in such insemination procedures whether or not such sperm cells are separated into enriched X chromosome bearing or Y chromosome bearing sperm cells.

Naturally, further significant objects and goals of the invention are disclosed and clarified in the proceeding description of the invention.

Accordingly, to achieve the various objects and goals of the invention, the present invention in one embodiment is a method of sperm cell processing, and the steps provided as obtaining sperm cells, cryopreserving the sperm cells, thawing the sperm cells, processing the sperm cells; and cryopreserving the sorted sperm cells. A further embodiment of the invention is a method of producing a mammal, comprising the method steps of obtaining sperm cells, cryopreserving the sperm cells, thawing the sperm cells, sorting the sperm cells, cryopreserving the sorted sperm cells, thawing the sorted cryopreserved sperm cells, inseminating at least one egg with the sorted cryopreserved sperm cells, fertilizing the at least one egg, and producing a mammal from the at least one fertilized egg.

Furthermore, to achieve the various objects and goals of the invention, the present invention is directed to embodiments providing for artificial insemination (in vivo) and in vitro fertilization procedures. Additionally embodiments may be further directed to the production of mammals or mammalian embryo, and may further be directed to establishing sperm samples such as straws, pellets, or the like, and the processing of semen.

Additional embodiments of the invention are disclosed throughout the description of the invention and in the following claims.

BRIEF DESCRIPTION OF THE DRAWINGS

Each Figure contained in each of the applications set out in Exhibit A are to be considered hereby incorporated by reference as part of this description of the instant invention.

DETAILED DESCRIPTION OF THE PREFERRED EMBODIMENTS

The present invention discloses semen and sperm cell processing and preservation techniques and systems of preservation, stimulation, fertilization, and insemination, addressing one or more sperm cell characteristics or sperm quality, such as sperm cell viability, motility, functionality, stimulation, and preservation, as well as fertility rates, insemination rates, fertilization rates. Further, sperm cell characteristics or sperm quality may be addressed within the context of various processing techniques, such as collection, handling, separation, storage, transportation, usage, fertilization, or insemination techniques.

Sperm cell quality may refer to any one or a combination of the various attributes of sperm cells previously mentioned or further mentioned herein, such as, for example, viability, motility, functionality, stimulation, and preservation of the sperm, or fertility rates, insemination rates, or fertilization rates corresponding to the sperm (such as in the fertility of the sperm). Sperm cell characteristic may refer to any one or a combination of various biological, chemical, physical, physiological, or functional attributes of one or more sperm cells, such as chromosome bearing attributes of the cell, or in some embodiments may refer to sperm cell quality as previously described.

Semen or sperm cell processing techniques may refer to any one or a combination of preservation, stimulation, insemination, fertilization, sorting, selection, separation, or thawing, and may be specifically directed to any one or a combination of collection, handling, selection, storage, transportation, usage, fertilization, or insemination techniques.

Sperm samples may refer to a volume containing sperm cells, potentially including semen, carrier fluid or other materials, and may comprise a pellets, straws, or other known forms of sperm samples.

Maintaining or Enhancing the Sperm Quality

Sperm cells may be maintained or enhanced in accordance with the present invention, and in some embodiments through sperm processing, such as through sperm cell sorting and preservation, and in accordance with fertilization and insemination techniques. Embodiments may provide preservation of the sperm or sperm cells, or other techniques as may be disclosed in the previously mentioned patent applications and the references listed in the List of References to be Incorporated by Reference, each application and reference expressly incorporated by reference to the extent consistent with the present description, and as further described below.

Sperm cells may also be maintained or enhanced in some embodiments by preservation and stimulation techniques as further described below, and also in further combination with the processing, stimulation, preservation, fertilization, and insemination techniques in the previously mentioned patent applications and the references listed in the List of References to be Incorporated by Reference.

Figure 1:
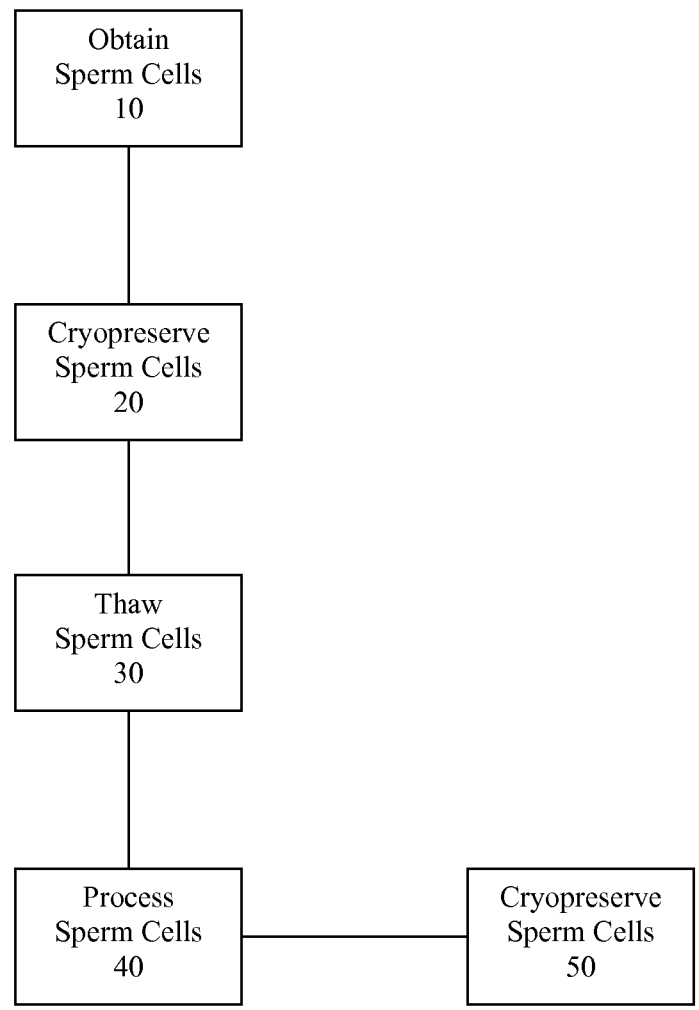
FIG. 1 is a flow diagram for one embodiment of the present invention.

Accordingly, the present invention may provide a method of sperm cell processing. FIG. 1 shows one process for sperm cell processing in accordance with the present invention. As shown, the sperm cells may be obtained 10 from a mammalian source, either directly or in various combinations of steps, such as through a storage facility. The sperm cells may be cryoperserved 20, as further described below. Subsequently, the sperm cells may be thawed 30. Further processing 40, further described below, may then be performed on the sperm cells prior to another cryopreservation of the sperm cells.

Figure 2:
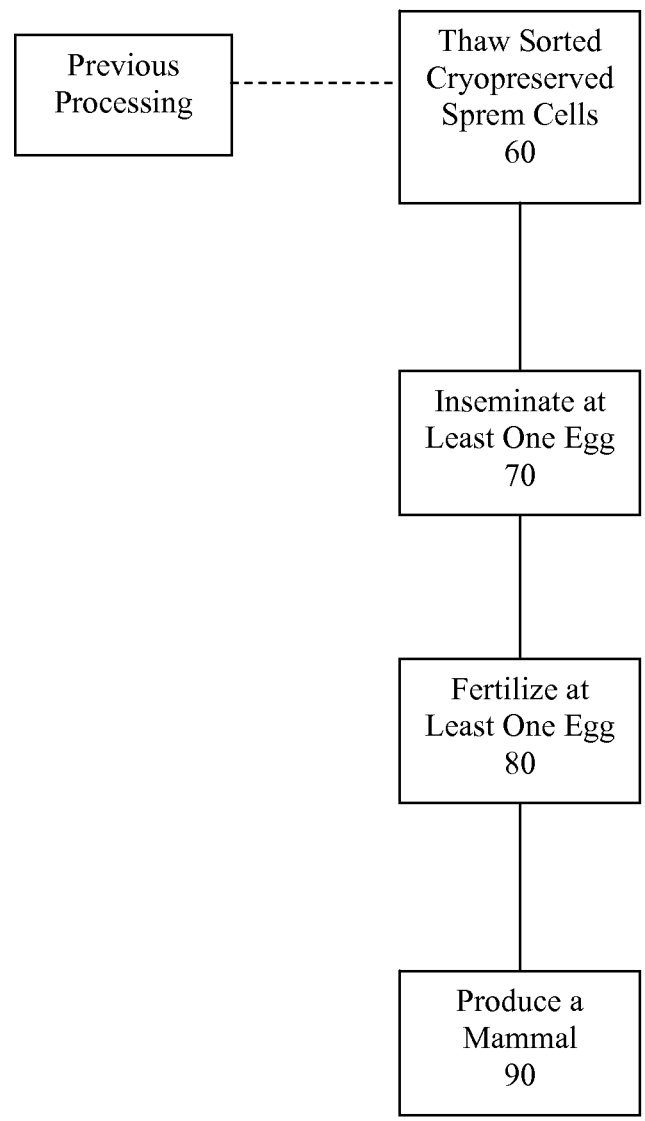
FIG. 2 is a flow diagram for a second embodiment of the present invention, potentially provided in combination with the embodiment of FIG. 1, in some embodiments.

Sperm cell processing, generally, and the process previously described may be conducted for insemination and fertilization. Therefore, an embodiment of the present invention may provide a method of producing a mammal, as shown in FIG. 2. After proceeding with previous processing, or in some embodiments as proceeding with the features 10, 20, 30, 40, and 50, the insemination of the mammal may performed. In one embodiment, the cryopreserved sperm cells may be thawed 60 and the insemination 70 and fertilization 80 of at least one egg with the sperm cells may be conducted. A mammal may then be produced 90 from the egg fertilized by the cryopreserved, processed, cryopreserved, and thawed sperm cells.

Furthermore, embodiments further support in vivo and in vitro techniques. Accordingly, a female of the species of the mammal from which sperm was obtained may be inseminated with the previously processed sperm cells, such as sorted and cryopreserved sperm cells as previously described. At least one egg of the female may then be fertilized and a mammal produced from the at least one fertilized egg. In accordance with in vitro procedures, after insemination and fertilization of at least one egg, a mammalian embryo may be produced, potentially developing into a mammal.

Each of the embodiments previously described may be considered departures from traditional sperm cell processing and the production of mammals and mammalian embryo. It has been traditionally viewed that such processing of sperm cells could not sufficiently ensure sperm quality or provide adequate rates of fertility, insemination, fertilization, or pregnancy. However, and as been taught in the various references cited herein and incorporated by reference, sperm cells may in fact be processed to achieve, for example, the sorting of sperm cells, potentially to differentiate sperm cells as either X chromosome bearing or Y chromosome bearing sperm cells, in some instances to provide for preselection of the sex of a mammal or mammalian embryo. The present invention also provides for such processing, and in some preferred embodiments, additional features of preservation heretofore traditionally thought not to be feasible commercially, or even possible, and heretofore providing a solution to those previously identified but unaddressed issues.

Obtaining Sperm

Semen, and in particular sperm cells, may be obtained and otherwise heretofore processed from mammals in accordance with the present invention such as equids, bovids, felids, ovids, canids, buffalo, oxen, elk, or porcine, or other mammal species. Further, some embodiments may provide obtaining and processing semen or sperm cells from prized mammal species, endangered mammal species, rare individuals of a mammal species, and even from zoological specimens or individuals. The resulting mammal or mammalian embryo may be produced in accordance with the techniques as previously described and as further described below. Sperm samples may be established, in some embodiments, as previously described.

Sample Preservation

Sperm samples are cryopreserved, such as by freezing, using various preservation techniques, such as freezing in a Hepes-buffered crydiluent. Sperm cells may be provided as pellets or straws and may be thawed using various thawing techniques, for example, with ram spermatozoa. Other sperm samples may be provided throughout the processing of sperm cells, and may or may not be cryopreserved when established as a sperm sample or when provided to inseminate or fertilize an egg.

One or more additives, singularly or in combination, may be introduced into the semen, sperm cells, or sperm sample. In one embodiment, a cryodiluent may be introduced into the sperm sample to preserve the sperm cells. The introduction of the additive or additives, such as a cryodiluent, into the sperm sample, and in some embodiments with as a cryopreservation step, potentially referred to as freezing, may maintain or enhance sperm cells, and may further maintain or enhance sperm quality, sperm cell quality, such as sperm cell viability, motility, functionality, stimulation, and fertility rates, and potentially one or more sperm cell characteristics. In other embodiments of the present invention, an additive or additives, such as cryodiluent, singularly or in combination, could be removed from the sperm sample. The removal of the cryodiluent or other additives from the sperm sample, and in some embodiments with cryopreservation steps, may maintain or enhance sperm cells, and may further maintain or enhance sperm quality, such as maintaining or enhancing sperm cell viability, motility, functionality, fertility rates, and potentially one or more sperm cell characteristics.

Sperm Processing

Sperm cells may also be maintained or enhanced in some embodiments of the present invention as part of sperm processing techniques, and sperm quality may further be maintained or enhanced, such as maintaining or enhancing sperm cell viability, motility, functionality, and potentially one or more sperm cell characteristics. Accordingly, in some embodiments, the sperm sample may be preserved, as previously described, such as through cryopreservation, such as freezing, or other preservation techniques such as those disclosed in the previously mentioned patent applications and the references listed in the List of References to be Incorporated by Reference.

Accordingly, cryodiluent or other additives, singularly or in combination, may be introduced into the sperm sample to preserve or stimulate the sperm. In one preferred embodiment, the introduction of the cryodiluent or other additives into the sperm sample contributes to the preservation of the sperm through cryopreservation, freezing the sperm sample, and therefore maintaining or enhancing the sperm cells, and further maintaining or enhancing sperm quality, such as maintaining or enhancing sperm cell viability, motility, functionality, and potentially one or more sperm cell characteristics. As previously mentioned, the cyrodilutent or other additives may be introduced into the sperm sample prior to sample preservation or as sample preservation. The sample may then be processed such as through collection, handling, separation, storage, transportation, usage, fertilization, or insemination techniques as disclosed in the previously mentioned patent applications and the references listed in the List of References to be Incorporated by Reference.

In one embodiment, cryodiluent or other additives, singularly or in combination, may be introduced into a sperm sample previously collected and the sample cryopreserved, such as through freezing, and followed by a thaw of the sample and subsequent processing, including collection, handling, separation, storage, transportation, usage, fertilization, or insemination processing techniques. One such processing step may be provided as sorting, and in some embodiments as the separation of X chromosome bearing sperm cells from Y chromosome bearing sperm cells, potentially into a high purity population sample or samples. Various benefits may be achieved through such a sperm processing technique. For example, various methods of sorting as described in the previously mentioned patent applications achieve a separation of X chromosome bearing sperm cells from Y chromosome bearing sperm cells while minimizing damage to the viable sperm cells. Further, non-viable sperm, contamination, or crydiluent or other additives, for example, may be eliminated through such separation techniques. Additionally, other aspects of sperm quality may be maintained or enhanced, particularly that of sperm cell motility and functionality. The sperm sample may further be stimulated during the processing to maintain or enhance sperm quality as previously described. One such method of sperm processing known in the art is described in U.S. Pat. No. 5,135,759, hereby incorporated by reference in this description, disclosing a flow cytometer sorting technique.

The processing of sperm cells may be performed by sorting the sperm cells as previously described, or in some embodiments, accordance with the following process. Sorting may comprise, in some embodiments, as a selecting of sperm cells based upon at least one desired characteristic, potentially sperm cell quality characteristics, such as viability, motility, functionality, stimulation, and preservation, or one or a combination of various sperm cell characteristics such as biological, chemical, physical, physiological, or functional attributes of one or more sperm cells, such as chromosome bearing attributes of the cell. The sperm cells may be stained, preferably with Hoechst 33342 or like stain or dye, or in combination with such stains or dyes, and the sperms cells differentiated based upon the staining and selection. The cells may then be separated based upon the differentiation and collected. The sperm cells may be so processed in accordance with the various techniques of those references cited herein and expressly incorporated by reference.

Example—Preserving and Processing Sample

In one embodiment of a preserving and processing technique, 200 µl of thawed spermatozoa was placed onto a 2 ml separation gradient (90%:45%) of PURESPERM™, a sterile colloidal silica suspension in an isotonic salt solution, a human preparation, and a Tris based diluent. The gradient preparations were then centrifuged at 1000 g for 15 minutes. The post PURESPERM™ pellet was removed, slowly diluted 1:4 with warm Tris based diluent and centrifuged at 650 g for 3 minutes. The supernatant was removed and the sperm stained, incubated and sorted as previously described. The Tris based diluent was used as the staining medium and ANDROHEP® (Minitub, Germany) plus 20% egg yolk was used as the collection medium.

The above example is one of various embodiments of the inventive technique, providing preservation of sperm, such as through cryopreservation or freezing, thawing the sperm, identifying the sperm, such as through staining, and sorting the sperm, such as into X and Y chromosome bearing populations.

Although the previous example provides a sperm preservation technique and processing technique of sperm collection, preservation, thaw and separation, other techniques are encompassed by and explicitly disclosed in the present invention. For example, one or a combination of various collection, handling, separation, storage, transportation, usage, fertilization, or insemination techniques may be performed as part of this present inventive technique. In one embodiment, sperm may be collected, followed by separation of X chromosome bearing sperm cells from Y chromosome bearing sperm cells. A preservation step prior to sperm cell separation may not be needed, for example, during circumstances in which the sorter apparatus is readily available after sperm collection. The sorted sperm sample or samples may then be preserved as an additional step and as previously described, potentially for further handling, separation, storage, transportation, usage, fertilization or insemination. The sorted sperm sample may further be stimulated during the processing to maintain or enhance sperm quality as previously described. The next example describes one example of a processing technique.

Example—Processing Samples

Sorted samples were centrifuged at 700 g for 6 min. at room temperature (24 C). The supernatant was removed and the sorted sperm could be used "fresh" for AI or in an IVF system; or the remaining pellet was extended 1:4 with the Hepes based cryodiluent, potentially the same diluent used for an original cryopreservation of the sperm, and frozen using various techniques, such as those previously described and as described below. The re-frozen and sorted sperm were thawed using methods such as a glass tube shaken in a 37° C. waterbath, and then could be used in an AI or IVF system.

Example—Processing Samples

The use of spermatozoa sorted from frozen-thawed pellets in the ovine mammal regarding in vitro fertilization systems. Frozen-sorted and frozen-sorted-frozen sperm used in an ovine IVF system were slowly diluted with 0.5 ml of IVF media, and in some embodiments, using ovine IVF protocol, and centrifuged in a Falcon tube with a tight lid at 300 g for 6 minutes. The supernatant was removed and the remaining sperm quickly placed in the IVF well at a concentration of one million motile sperm/ml. Preferably, a high standard of media preparation (i.e. use of eggs less than 24 hours old, ultracentrifugation of egg yolk diluents and meticulous filtering) and handling of the samples (i.e. constant temperature) is required.

Other preservation, processing, fertilization, and insemination techniques need not include a separation step. For example, the sperm may be collected, followed by a preservation step and subsequent handling, storage, transportation, usage, fertilization, or insemination.

Furthermore, one or more preservation steps may be conducted as part of preservation, processing, fertilization, and insemination techniques, or combinations thereof, such preservation in some embodiments comprising cryopreservation, such as through freezing of the sperm sample, and subsequent steps of thawing, occurring before, concurrent with, or after one or more other processing techniques.

Example—Sex-Sorting and Re-Cryopreservation of Frozen-Thawed Ram Sperm for In Vitro Embryo Production Application of sperm sorting to breeding of livestock and wildlife may be limited when the sorter is a long distance from the male(s), as previously described, but would be facilitated by the sorting of cryopreserved and thawed sperm, such as frozen-thawed sperm (Lu K H et al., Theriogenology 1999:52:1393-1405) and cryopreserving or re-freezing it. High purity sorting with maintained quality of frozen-thawed ram sperm may be achieved after processing to remove the cryodiluent. The aim of this study was to evaluate the functional capacity of frozen-thawed sperm after sorting and a second cryopreservation/thawing step. Frozen semen from 2 rams (n=2 ejaculates per ram) was used throughout. Post-thaw sperm treatments comprised (i) unsorted (Control); (ii) sorted (Frozen-Sort) and (iii) sorted then re-frozen (Frozen-Sort-Frozen). X and Y sperm were separated using a high-speed sorter (SX MoFlo(R), Cytomation, Colo., USA) after incubation with Hoechst 33342 and food dye to eliminate non-viable sperm. Reanalysis revealed high levels of purity for X- and Y-enriched samples for all treatments (87.0+/−4.5%). For IVF, 472 IVM oocytes were inseminated with 1×10(6) motile sperm/mL. After 3 h in SOF medium, oocytes were transferred to Sydney IVF cleavage medium (Cook(R), QLD, Australia) for 4 d followed by Sydney IVF blastocyst medium (Cook(R)) for an additional 3 d culture in 5% O2:5% CO2:90% N2. Oocytes were assessed for cleavage at 24 and 48 h post-insemination (p.i.). At 52 h p.i., uncleaved oocytes were stained with orcein for assessment of maturation and fertilization. Data from 3 replicates were analyzed by ANOVA, Chi-square and Fisher Exact Test. At insemination, % motile sperm (+/− SEM) was higher (P<0.001) for Frozen-Sort (85.8+/−2.4%)

and Frozen-Sort-Frozen (66.7+/−7.7%) than Control (36.7+/−2.1%). Maturation rate was 95.6% (451/472). Cleavage of oocytes in a parthenogenetic control group (no sperm) was low (2/56; 3.6%). Polyspermic fertilization was low (9/451; 2.0%) and did not differ among treatments.

TABLE 1

Fertilization & early embryo development of oocytes after incubation with frozen-thawed unsorted (Control), frozen-thawed & sorted (Froz-Sort) & frozen-thawed, sorted then frozen-thawed (Froz-Sort-Froz) ram sperm. Values in parentheses are percentages.

| Treatment | No. of mature oocytes fertilized[d] | No. of mature oocytes undergoing cleavage after insemination | | No. of cleaved oocytes forming blastocysts | | |
|---|---|---|---|---|---|---|
| | | 24 h | 48 h | Day 5 | Day 6 | Day 7 |
| Control | 40 (67.8) | 26 (44.1) | 36 (61.0) | 4 (11.1) | 13 (36.1) | 16 (44.4)[a] |
| Froz-Sort | 110 (63.6) | 67 (38.7) | 109 (63.0) | 24 (22.1) | 34 (31.2) | 57 (52.3)[ab] |
| Froz-Sort-Froz | 94 (57.7) | 71 (43.6) | 91 (55.8) | 23 (25.3) | 347 (40.7) | 59 (64.8)[bc] |

[d]Monospermic fertilization. Within column, values with different superscripts differ (P < 0.05).

Fertilization and cleavage rates were consistently high across treatments. Blastocyst development rate was higher for oocytes fertilized with Froz-Sort-Froz than with Control sperm. These results demonstrate that frozen-thawed ram sperm can be sex-sorted for either immediate or future use in an IVF system after re-cryopreservation.

The above example is one of various embodiments of the inventive technique, providing preservation of sperm, such as through cryopreservation, such as freezing, thawing the sperm, sorting the sperm, such as into X and Y chromosome bearing populations, preserving the sorted sample, such as through cryopreservation or freezing, and further including thawing the sperm sample for use, such as for fertilization or insemination.

Consideration should be given to fertility rates respective of preservation and processing procedures, such as separation for sex-sorting and cryopreservation of sperm samples, as the next Example describes, and in combination with cryopreservation, thawing, processing, and subsequent cryopreservation, as disclosed in this description.

Example—Effect of Dose of Sperm Processed for Sex-Sorting and Crypreservation on Fertility in Ewes Lambs have been produced after artificial insemination (AI) with low numbers (2-4×10$^6$) of cryopreserved sex-sorted sperm. Fewer ewes were pregnant after AI with X- or Y-sorted frozen-thawed (25%, 15% respectively) than with a commercial dose of unsorted frozen-thawed sperm (54%). The object of the present study was to determine the minimum numbers of sorted frozen-thawed sperm required to obtain pregnancy rates similar to those obtained with unsorted sperm.

A sample of sperm from single ejaculates of 2 rams was stained, incubated, analyzed and sorted using a modified high speed cell sorter (MoFlo®, Cytomation, Fort Collins, Colo., USA) as previously described. Sperm were processed at 15,000-18,000/serc without sex-sorting into 10 ml centrifuge tubes pre-soaked with 1% BSA in sheath fluid containing 0.2 ml Tris-buffered medium and 20% egg yolk (v/v). For every sample, 1.3×10$^6$ sperm were sex-sorted and analyzed to determine purity. Sorted and unsorted (control) samples were extended with a zwitterions-buffered diluent containing 13.5% egg yolk and 6% glycerol and frozen as 250 ul pellets containing 5×10$^6$ sperm. The time of estrus was controlled in 144 Merino ewes by progestagen sponges (FGA, Vetrepharm A/Asia, Sydney) inserted intravaginally for 12 days and an injection of 400 I.U of PMSG (Pregnecol, Vetrepharm A/Asia) at sponge removal (SR). Thirty-six h after SR 134 ewes were injected with 40 μg GnRH (Fertagyl®, Intervet) to control the time of ovulation. One hundred and eleven ewes were inseminated in the uterus by laparoscopy 57-60 h after SR with 5, 10, 20 or 40×10$^6$ sorted or unsorted frozen-thawed sperm. Thirteen ewes not given GnRH were inseminated with a commercial dose of unsorted frozen-thawed sperm. Thirteen ewes not given GnRH were inseminated with a commercial dose of unsorted frozen-thawed sperm 57-58 h after SR. Pregnancy was diagnosed by ultrasound on d53. The data were analyzed by Chi-square.

Sperm motility after thawing was 37.8+/−1.78% (sorted) and 42.9+/−0.93% (unsorted). Seven of 13 (53.8%) ewes not given GnRH were pregnant. Of the GnRH-treated ewes the proportion pregnant was affected by the number of sperm inseminated (p<0.05) but not by ram or type of sperm (p>0.05). For ewes inseminated with sorted or unsorted (control) frozen-thawed sperm, pregnancy rate was higher for inseminates of 10 and 40×10$^6$ than for 5 and 20×10$^6$ sperm (Table 1). The results suggest that a minimum of 40×10$^6$ sorted frozen-thawed sperm inseminated close to the time of ovulation are required to obtain commercially acceptable pregnancy rates.

TABLE 1

Pregnancy after intrauterine insemination of ewes with frozen-thawed control and sorted ram sperm.

| Dose (×10$^6$ sperm) | No. ewes inseminated | No. ewes pregnant | % ewes pregnant |
|---|---|---|---|
| 5 | 30 | 10 | 33.3[a] |
| 10 | 28 | 16 | 57.1[b] |
| 20 | 29 | 10 | 34.5[a] |
| 40 | 23 | 16 | 69.6[a] |

[ab]Within columns different superscripts differ (p < 0.05).
[a]This research was supported by XY, Inc; CO, USA; The Australian Research Council, Vetrephann A/Asia.

The invention can further include a sperm sample, such as a straw, and in some embodiments straws utilized in IVF, produced in accordance with any of the above described embodiments of the invention, such as any of the processing, stimulation, preservation, fertilization, and insemination techniques, and be of maintained or enhanced sperm quality, such as a straw of desired viability, motility, functionality, or other characteristics, or combinations of characteristics, potentially resulting in desirable levels of fertility rates, and in some embodiments, particularly for equine mammals. The sperm sample or straw may be particularly suited for individual production embryos.

The invention can further include a mammal produced in accordance with any of the above described embodiments of the invention, or can include a mammal of predetermined sex in accordance with the various embodiments of the invention that provide sperm cell insemination samples having an enriched population of either X-chromosome bearing sperm cells or enriched population of Y-chromosome bearing sperm cells, or a mammal produced in accordance with any embodiment of the invention in which a sperm cell insemination sample containing a low number of sperm cells compared to the typical number used to inseminate that particular species of mammal is used, or elk progeny produced in accordance with the invention as described above.

The invention further includes various processing, preservation, stimulation, fertilization, and insemination techniques as disclosed herein and as disclosed in the previously mentioned patent applications and references. Accordingly, the various semen and sperm cell processing systems and systems of preservation, stimulation, fertilization, and insemination, embodiments, in various embodiments addressing sperm quality such as one or more sperm cell characteristics, such as viability, motility, functionality, or fertilization rates consistent with the disclosures of the previously mentioned patent applications and references. Further, sperm cell characteristics may be addressed within the context of various collection, handling, separation, storage, transportation, usage, fertilization, or insemination techniques, and in those or other various embodiments, within the context of assaying, testing, or determining the biological, chemical, physical, physiological, or functional attributes of sperm cells. Therefore, systems of the present invention may provide sperm cell processing, stimulation, preservation, fertilization, and insemination, for example, incorporating flow sorting techniques, high purity separation techniques, low dose fertilization and insemination techniques, heterospermic insemination procedures, such as to assess comparative viability, motility, function, or fertility processed in various pressure environments within a sorter, as but a few examples.

The disclosure incorporated by reference, such as the various examples provided of separating X chromosome bearing sperm cells from Y chromosome bearing sperm cells, and other disclosed techniques of collection, handling, separation, storage, transportation, usage, fertilization, and insemination are not meant to limit the present invention to any particular embodiment, whether apparatus, method, or otherwise. The descriptions incorporated by reference and the various examples should not be construed to limit the present invention to only techniques for sperm sorting or only techniques for sperm preservation. This disclosure, however, may be understood to incorporate the various techniques in the context of the various embodiments of the present invention. Further, the present invention should be considered to incorporate such techniques of sperm processing, preservation, stimulation, fertilization, and insemination consistent with the features disclosed.

As can be easily understood from the foregoing, the basic concepts of the present invention may be embodied in a variety of ways. It involves both a sperm cell process system including both techniques as well as devices to accomplish sperm cell processing. In this application, various sperm cell processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood as encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered as encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "cryopreserver" should be understood to encompass disclosure of the act of "cryopreserving"—whether explicitly discussed or not—and, conversely, were there effectively disclosure of the act of "cryopreserving", such a disclosure should be understood to encompass disclosure of a "cryopreserver" and even a "means for cryopreserving." Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing methods as herein disclosed and described, ii) the related systems, devices, and multiple apparatus disclosed and described, iii) similar, equivalent, and even implicit variations of each of these systems and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented.

The Applicant may have presented claims with an set of initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

What is claimed is:

1. A method of producing a non-human mammalian embryo comprising:
   obtaining sperm cells;
   cryopreserving the sperm cells;
   thawing the cryopreserved sperm cells;
   staining the thawed sperm cells;
   sorting the thawed sperm cells into X chromosome-bearing and/or Y chromosome bearing subpopulations by flow cytometry;
   establishing at least one sperm sample from the sorted sperm cells;
   cryopreserving the sorted sperm sample; and
   establishing an increased blastocyst development rate using motile sperm cells from the cryopreserved sorted sperm sample compared to the blastocyst development rate using the obtained sperm cells.

2. The method of claim 1, further comprising the step of producing a viable non-human mammal from the mammalian embryo.

3. The method of claim 1, wherein the step of fertilizing at least one egg with the thawed, twice cryopreserved sperm cells through artificial insemination or in vitro fertilization further comprises fertilizing the at least one egg through artificial insemination.

4. The method of claim 3, wherein the step of fertilizing the at least one egg through artificial insemination further comprises inseminating a superovulated female with the thawed, twice cryopreserved sperm cells.

5. The method of claim 1, wherein the step of fertilizing at least one egg with the thawed, twice cryopreserved sperm cells through artificial insemination or in vitro fertilization further comprises fertilizing the at least one egg in vitro.

6. The method of claim 1, further comprising the step of transferring the at least one fertilized egg to a recipient female.

7. The method of claim 1, further comprising the step of obtaining at least one egg of a superovulated female of a species of the mammal and wherein the step of fertilizing includes fertilizing the at least one egg in vitro.

8. The method of claim 7, wherein the step of fertilizing the at least one egg in vitro further comprises fertilizing more than one egg in vitro.

9. The method of claim 7, further comprising the step of transferring the at least one fertilized egg to a recipient female.

10. The method of claim 1, wherein the second cryopreserving step includes cryopreserving the at least one sperm sample at a concentration and dosage appropriate for artificial insemination or in vitro fertilization.

11. The method of claim 1, wherein the step of establishing at least one sperm sample further comprises establishing a sample of the sorted, thawed sperm cells capable of fertilizing at least one egg of the female non-human mammal.

12. The method of claim 1, wherein the step of establishing at least one sperm sample further comprises establishing a sample of the sorted, thawed sperm cells capable of fertilizing at least one egg of a superovulating female non-human mammal.

13. The method of claim of 1, wherein the step of establishing at least one sperm sample further comprises establishing a sample of the sorted, thawed sperm cells capable of fertilization in vitro of at least one egg.

14. The method of claim 1, further comprising the step of fertilizing a plurality of eggs of a female non-human mammal.

15. The method of claim 1, further comprising the step of producing at least one animal of a pre-selected sex from the cryopreserved processed sperm cells.

16. The method of claim 1, wherein the twice cryopreserved sperm cells have a pre-selected sex.

17. The method of claim 1, wherein the twice cryopreserved sperm cells include a sperm sample selected from the group consisting of: a straw, a pellet, an insemination dose, and a prepared sperm sample.

* * * * *